US011033640B2

(12) United States Patent
Yeh et al.

(10) Patent No.: US 11,033,640 B2
(45) Date of Patent: Jun. 15, 2021

(54) ENTERIC CT CONTRAST MATERIAL BASED ON LOW-Z ATOMS

(71) Applicant: THE REGENTS OF THE UNIVERSITY OF CALIFORNIA, Oakland, CA (US)

(72) Inventors: Benjamin M. Yeh, Hillsborough, CA (US); Yanjun Fu, San Francisco, CA (US); Tejal Desai, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 203 days.

(21) Appl. No.: 14/215,827

(22) Filed: Mar. 17, 2014

(65) Prior Publication Data
US 2014/0276021 A1 Sep. 18, 2014

Related U.S. Application Data

(60) Provisional application No. 61/790,734, filed on Mar. 15, 2013, provisional application No. 61/798,392, filed on Mar. 15, 2013.

(51) Int. Cl.
A61K 49/04 (2006.01)
A61B 6/00 (2006.01)
A61B 6/03 (2006.01)

(52) U.S. Cl.
CPC ...... A61K 49/0414 (2013.01); A61K 49/0419 (2013.01); A61K 49/0461 (2013.01); A61B 6/032 (2013.01); A61B 6/481 (2013.01)

(58) Field of Classification Search
None
See application file for complete search history.

(56) References Cited

U.S. PATENT DOCUMENTS

| | | | |
|---|---|---|---|
| 3,592,185 A | 7/1971 | Frei et al. | |
| 4,615,879 A | 10/1986 | Runge et al. | |
| 5,205,290 A | 4/1993 | Unger | |
| 5,380,514 A | 1/1995 | Waigh et al. | |
| 5,472,682 A | 12/1995 | Ruddy et al. | |
| 5,550,263 A * | 8/1996 | Hersl of | C07F 9/10 424/9.45 |
| 5,580,579 A * | 12/1996 | Ruddy | A61K 9/146 424/489 |
| 6,818,199 B1 * | 11/2004 | Hainfeld | A61K 47/48053 424/1.11 |
| 2007/0258907 A1 | 11/2007 | Davis | |
| 2008/0233052 A1 * | 9/2008 | Axelsson | A61K 33/24 424/9.42 |
| 2009/0297441 A1 * | 12/2009 | Canham | A61K 49/0043 424/1.61 |

FOREIGN PATENT DOCUMENTS

| | | |
|---|---|---|
| EP | 2127682 A1 | 12/2009 |
| GB | 1174366 A | 12/1969 |
| JP | 63-255237 | 10/1988 |
| JP | H05-508387 T | 11/1993 |
| JP | H06-321865 A | 11/1994 |
| JP | H07-509716 T | 10/1995 |
| JP | H09-512029 T | 12/1997 |
| JP | H10-500691 T | 1/1998 |
| JP | 2000-504742 T | 4/2000 |
| JP | 2003-160512 | 6/2003 |
| JP | 2009-508924 A | 3/2009 |
| WO | WO 1991/014457 | 10/1991 |
| WO | WO 1992/017514 | 10/1992 |
| WO | WO 1994/003107 | 2/1994 |
| WO | WO 1995/032005 | 5/1995 |
| WO | WO 1995/022995 | 8/1995 |
| WO | WO 1995/028969 | 11/1995 |
| WO | WO 1997/030736 | 8/1997 |
| WO | WO 2007/034196 | 3/2007 |

(Continued)

OTHER PUBLICATIONS

Van Schooneveld et al. A fluorescent, paramagnetic and PEGylated gold/silica nanoparticle for MRI, CT and fluorescence imaging. 2010 Contrast Media Mol. Imaging 5: 231-236.*

Abuchowski, A. et al., "Effect of Covalent Attachment of Polyethylene Glycol on Immunogenicity and Circulating Life of Bovine Liver Catalase." *The Journal of Biological Chemistry*, vol. 252, Bi, 11, pp. 3582-3586 (1977).

Abuchowski, A. et al., "Cancer Therapy With Chemically Modified Enzymes. I. Antitumor Properties of Polyethylene Glycol-Asparaginase Conjugates." *Cancer Biochem. Biophys.*, vol. 7, pp. 175-186 (1984).

Beauchamp, C. et al., "A New Procedure for the Synthesis of Polyethylene Glycol-Protein Adducts; Effects on Function, Receptor Recognition, and Clearance of Superoxide Dismutase, Lactoferrin, and $\alpha_2$-Macroglobulin." *Analytical Biochemistry*, vol. 131, pp. 25-33 (1983).

Berger and Pizzo, "Preparation of Polyethylene Glycol-Tissue Plasminogen Activator Adducts That Retain Functional Activity: Characteristics and Behavior in Three Animal Species." *Blood*, vol. 71, No. 6, pp. 1641-1647 (1988).

(Continued)

*Primary Examiner* — Jennifer Lamberski
(74) *Attorney, Agent, or Firm* — Morgan, Lewis & Bockius LLP; Jeffry S. Mann

(57) ABSTRACT

The present invention provides particulate contrast media for use in CT imaging. In an exemplary embodiment, the invention provides an enteric contrast medium formulation based on particles of low-Z elements selected from microparticles and nanoparticles. In various embodiments, the particles are coated with a material compatible with enteric administration of the formulation to a subject in need of such administration. The invention also provides methods for imaging of body parts simultaneously enhanced with contrast media of the invention and with other contrast media of a different type using CT imaging, including dual energy or spectral CT imaging. The invention also provides methods for the digital separation of CT signal produced by the contrast media of the invention from the CT signal produced by other contrast media or bodily tissues, to generate multiple resultant CT images with individual contrast materials subtracted or highlighted.

11 Claims, 12 Drawing Sheets

(56) References Cited

FOREIGN PATENT DOCUMENTS

| WO | WO 2012/080260 | 6/2012 |
|---|---|---|
| WO | WO 2012/080290 | 6/2012 |
| WO | WO 2012/101524 | 8/2012 |
| WO | WO 2012/170569 | 12/2012 |
| WO | WO 2013/184061 | 12/2013 |
| WO | WO 2014/145509 A1 | 9/2014 |
| WO | WO 2015/024025 | 2/2015 |

OTHER PUBLICATIONS

Boccu, E. et al., "Coupling of Monomethoxypolyethyleneglycols to Proteins via Active Esters." *Z. Naturforsch.*, vol. 38c, pp. 94-99 (1983).

Bückmann and Morr, "Functinoalization of Poly(ethylene glycol) and Monomethoxy-Poly(ethylene glycol)." *Makromol. Chem.*, vol. 182, pp. 1379-1384 (1981).

Byun, Y. et al., "Binding Kinetics of Thrombin and Antithrombin III with Immobilized Heparin Using a Spacer." *ASAIO Journal*, M649-M653 (1992).

Cohn and Younes, "Biogadable PEO/PLA block copolymers." *Journal of Biomedical Materials Research*, vol. 22, pp. 993-1009 (1988).

Delgado, C. et al., "Coupling of Poly(ethylene glycol) to Albumin under Very Mild Conditions by Activation with Tresyl Chloride: Characterization of the Conjugate by Partitioning in Aqueous Two-Phase Systems." *Biotechnology and Applied Biochemistry*, vol. 12, pp. 119-128 (1990).

Jackson, C.C. et al., "Synthesis, Isolation, and Characterization of Conjugates of Ovalbumin with Monomethoxypolyethylene Glycol Using Cyanuric Chloride as the Coupling Agent." *Analytical Biochemistry*, vol. 165, pp. 114-127 (1987).

Joppich and Luisi, "Peptides Flanked by Two Polymer Chains, 1 Synthesis of Glycyl-L-tryptophylglycine Substituted by Poly(ethylene oxide) at both the Carboxy and the Amino End Groups." *Makromol. Chem.*, vol. 180, pp. 1381-1384 (1979).

Katre, N.V. et al., "Chemical modification of recombinant interleukin 2 by polyethylene glycol increases its potency in the murine Meth A sarcoma model." *Proc. Natl. Acad. Sci. USA*, vol. 84, pp. 1487-1491 (1987).

Kitamura, K. et al., "Chemical Engineering of Monoclonal Antibody A7 by Polyethylene Glycol for Targeting Cancer Chemotherapy." *Cancer Research*, vol. 51, pp. 4310-4315 (1991).

Koide and Kobayashi, "Modification of Amino Acids in Porcine Pancreatic Elatase With Polyethylene Glycol in Relation to Binding Ability Towards Anti-Serum and to Enzymic Activity." *Biochemical and Biophysical Research Communications*, vol. 111, No. 2, pp. 659-667 (1983).

Mongan, John et al., "In Vivo Differentiation of Complementary Contrast Media at Dual-Energy CT." *Radiology*, vol. 265, No. 1, pp. 267-272 (2012).

Murty, R.C., "Effective atomic numbers of heterogeneous materials." *Nature*, vol. 207, pp. 398-399 (1965).

Nilsson and Mosbach, "Immobilization of Ligands with Organic Sulfonyl Chlorides." *Methods in Enzymology*, vol. 104, pp. 56-69 (1984).

Veronese, F.M. et al., "Surface Modification of Proteins. Activation of monomethoxy-Polyethylene Glycols by Phenylchloroformates and Modification of Riobuclease and Superoxide Dismutase." *Applied Biochemistry and Biotechnology*, vol. 11, pp. 141-152 (1985).

Woghiren, C. et al., "Protected Thiol-Polyethylene Glycol: A New Activated Polymer for Reversible Protein Modification." *Bioconjugate Chem.*, vol. 4, pp. 314-318 (1993).

Yu and Watson, "Metal-Based X-ray Contrast Media." *Chem. Rev.*, vol. 99, pp. 2353-2377 (1999).

Zalipsky and Lee, "Use of Functionalized Poly(Ethylene Glycol)s for Modification of Polypeptides." *Poly(ethylene glycol) Chemistry: Biotechnical and Biomedical Applications*, Harris Ed., Plenum Press, NY, pp. 347-370 (1992).

Zalipsky, S. et al., "Evaluation of a New Reagent for Covalent Attachment of Polyethylene Glycol to Proteins." *Biotechnology and Applied Biochemistry*, vol. 15, pp. 100-114 (1992).

Cohn and Younes, "Biodegradeable PEO/PLA block copolymers" Journal of Biomedical Materials Reasearch, vol. 22, pp. 993-1009 (1988).

Gamarra et al., "Characterization of Superparamagnetic Iron Oxide Coated with Silicone Used as Contrast Agent for Magnetic Resonance Image for the Gastrointestinal Tract." Journal of Nanoscience and Nanotechnology, vol. 10, pp. 1153-1158 (2010).

Primak et al., "Improved dual-energy material discrimination for dual-source CT by means of additional spectral filtration." Am. Assoc. Phys. Med., vol. 36, No. 4, pp. 1359-1369 (2009).

Younes and Cohn, "Morphological study of biodegradable PEO/PLA block copolymers." Journal of Biomedical Materials Research, vol. 21, pp. 1301-1316 (1987).

Johnson et al., "Dual-energy CT for the evaluation of silicone breast implants." *Eur Radiol* 23:991-996 (2012).

Sahani et al., "Evaluation of Simethicone-coated Cellulose as a Negative Oral Contrast Agent for Abdominal CT." *Acad Radiol* 10:491-496 (2003).

Dekrafft et al., "Zr and Hf-based nanoscale metal-organic frameworks as contrast agents for computed tomography." J. Mater Chem., 22(35): 18139-44 (2012).

Piao et al., "Designed Fabrication of Silica-Based Nanostructure Particle Systems for Nanomedicine Applications." Adv. Func. Mater., 18, 3745-3758 (2008).

Nakamura et al., "Thiol-Organosilica Particles Internally Functionalized with Popidium Iodide as a Multicolor Fluorescence and X-ray Computed Tomography Probe and Application for Non-Invasive Functional Gastrointestinal Tract Imaging." Chem. Materials., ACS Publications., 24, 3772-3729 (2012).

Laurent et al., Magnetic Iron Oxide Nanoparticles: Synthesis, Stabilization, Vectorization, Physicochemical Characterizations, and Biological Applications. Chem. Rev. 108, 2064-2110 (2008).

Matsuoka et al., (Positive and Negative Oral Contrast Agents for Combined Abdominal and Pelvic Helical CT: First Iodinated Agent and Second Water. Radiat Med. Abstract; 18(3):213-6). (2000).

Fornaro et al., (Dual- and multi-energy CT: approach to functional imaging. Insights Imaging. Apr. 2011; 2(2): 149-159) (2011).

Fitzgerald et al., (CT Image Contrast of High Z Elements: Phantom Imaging Studies and Clinical Implications. Radiology. vol. 278, No. 3, 723-733 (2016).

\* cited by examiner

FIG. 7

| Atom Number (Z) | Atom Name | Contrast compounds as examples (including both anhydrous form and the hydrate form wherever applicable) | Note |
|---|---|---|---|
| 12 | Mg | magnesium orthoborate $Mg_3(BO_3)_2$<br>magnesium carbonate $MgCO_3$, $MgCO_3 \cdot 3H_2O$<br>magnesium basic carbonate $3MgCO_3 \cdot Mg(OH)_2 \cdot 3H_2O$ (hydromagnesite)<br>magnesium hydroxide<br>(only 4 mg dissolved in 100 g water even upon boiling)<br>magnesium phosphate<br>magnesium pyrophosphate $Mg_2P_2O_7$<br>magnesium orthosilicate $Mg_2SiO_4$ | MgO has also low water solubility but reacts with water, so not recommended. |
| 13 | Al | aluminum hydroxide<br>aluminum oxide<br>aluminum phosphate $AlPO_4$<br>aluminum silicate $Al_2O_3 \cdot SiO_2$, or $3Al_2O_3 \cdot 2SiO_2$ | |
| 14 | Si | silicon dioxide $SiO_2$<br>aluminum silicate $Al_2O_3 \cdot SiO_2$, or $3Al_2O_3 \cdot 2SiO_2$<br>calcium metasilicate $CaSiO_3$<br>calcium orthosilicate $Ca_2SiO_4$<br>magnesium orthosilicate $Mg_2SiO_4$<br>zinc silicate (meta or ortho form) $ZnSiO_3$ or $Zn_2SiO_4$ | |
| 15 | P | aluminum phosphate $AlPO_4$<br>calcium phosphate $Ca_3(PO_4)_2$<br>calcium pyrophosphate $Ca_2P_2O_7$<br>magnesium phosphate | |
| 20 | Ca | calcium carbonate<br>calcium phosphate<br>calcium pyrophosphate<br>calcium metasilicate $CaSiO_3$<br>calcium orthosilicate $Ca_2SiO_4$<br>calcium tartrate $CaC_4H_4O_6$ | |
| 21 | Sc | scandium hydroxide<br>scandium oxide | |
| 22 | Ti | titanium dioxide $TiO_2$ | |
| 26 | Fe | iron oxides $Fe_2O_3$ or $Fe_3O_4$ | Used already as MRI contrast; but very large doses are needed as enteric CT contrast thus the safety is unknown. |
| 30 | Zn | zinc aluminate $ZnAl_2O_4$<br>zinc carbonate<br>zinc gallate $ZnGa_2O_4$<br>zinc oxide<br>zinc phosphate<br>zinc pyrophosphate<br>zinc silicate (meta or ortho form) $ZnSiO_3$ or $Zn_2SiO_4$<br>zinc sulfide<br>zinc tartrate $ZnC_4H_4O_6$ | |
| 35 | Br | Perfluorooctyl bromide | Tested in clinical trials as ultrasound contrast agent, safety is unknown if large dose is applied as enteric CT contrast agent. |
| 38 | Sr | strontium carbonate<br>strontium phosphate<br>strontium silicate<br>strontium sulfate | |
| 39 | Y | yttrium hydroxide<br>yttrium oxide | |

FIG. 9

| Material | CT Number | | | | 80:140 kVp CT number ratio |
|---|---|---|---|---|---|
| | 80 kVp | 100 kVp | 120 kVp | 140 kVp | |
| Polyethylene | -130 | -130 | -118 | -108 | 1.20 |
| Copolymer | -160 | -150 | -140 | -135 | 1.19 |
| Vivak | 140 | 148 | 155 | 157 | 0.89 |
| Polypropylene | -140 | -130 | -125 | -124 | 1.13 |
| Polyethylene | -74 | -62 | -55 | -49 | 1.51 |
| Urethane | -8 | -6 | -9 | -6 | 1.25 |
| Polycarbonate rod | 81 | 97 | 99 | 110 | 0.74 |
| Polycarbonate board | 88 | 122 | 124 | 120 | 0.73 |
| Acrylic board | 223 | 182 | 161 | 170 | 1.31 |
| Teflon rod | 344 | 351 | 352 | 360 | 0.96 |
| Polyvinyl chloride board | 421 | 432 | 400 | 388 | 1.09 |
| Iohexol | 616 | 496 | 404 | 350 | 1.76 |
| 2.1% barium w/v | 572 | 453 | 389 | 327 | 1.75 |

FIG. 10

| Type of silica | Layer | CT Number | | | | 80:140 kVp CT number ratio |
|---|---|---|---|---|---|---|
| | | 80 kVp | 100 kVp | 120 kVp | 140 kVp | |
| Crystalline silica (original) | Supernatant | 407 | 353 | 334 | 314 | 1.30 |
| | Sediment | 982 | 882 | 827 | 783 | 1.25 |
| Coated (Version A) | Supernatant | 386 | 334 | 318 | 299 | 1.29 |
| | Sediment | 711 | 621 | 584 | 549 | 1.30 |
| Coated (Version B) | Supernatant | 402 | 353 | 334 | 318 | 1.26 |
| | Sediment | 657 | 583 | 550 | 520 | 1.26 |
| Fused (amorphous) silica (original) | Supernatant | 367 | 321 | 303 | 286 | 1.29 |
| | Sediment | 762 | 642 | 588 | 539 | 1.41 |
| Coated (Version A) | Nearly homogeneous | 329 | 287 | 266 | 250 | 1.32 |
| Coated (Version B) | Nearly homogeneous | 310 | 274 | 357 | 341 | 1.29 |
| Spherical amorphous silica (original) | Supernatant | 363 | 313 | 295 | 278 | 1.31 |
| | Sediment | 634 | 463 | 441 | 406 | 1.56 |
| Coated (Version A) | Nearly homogeneous | 356 | 312 | 293 | 276 | 1.29 |
| Coated (Version B) | Nearly homogeneous | 345 | 395 | 286 | 269 | 1.28 |

FIG. 11

| Material | CT scanner manufacturer | CT number | | | | 80:140 kVp CT number ratio |
|---|---|---|---|---|---|---|
| | | 80 kVp | 100 kVp | 120 kVp | 140 kVp | |
| Iohexol 8.75 mg I/mL | General Electric | 376 | 300 | 249 | 212 | 1.77 |
| | Siemens | 364 | 279 | 230 | 198 | 1.84 |
| Silica colloid | General Electric | 585 | 522 | 482 | 456 | 1.28 |
| | Siemens | 592 | 523 | 487 | 460 | 1.29 |
| Coated amorphous silica | General Electric | 355 | 312 | 385 | 267 | 1.33 |
| | Siemens | 357 | 315 | 390 | 271 | 1.32 |
| Readi-cat | General Electric | 572 | 459 | 382 | 328 | 1.74 |
| | Siemens | 570 | 451 | 376 | 326 | 1.75 |
| Magnesium hydroxide | General Electric | 661 | 616 | 585 | 564 | 1.17 |
| | Siemens | 667 | 614 | 585 | 573 | 1.16 |
| Amorphous spheric silica | General Electric | 366 | 326 | 299 | 280 | 1.31 |
| | Siemens | 377 | 323 | 302 | 291 | 1.30 |

# ENTERIC CT CONTRAST MATERIAL BASED ON LOW-Z ATOMS

CROSS-REFERENCE TO RELATED APPLICATIONS

This application claims priority to U.S. Provisional Patent Application No. 61/790,734 filed Mar. 15, 2013 and U.S. Provisional Patent Application No. 61/798,392 filed Mar. 15, 2013, the disclosure of each is incorporated herein by reference in its entirety for all purposes.

GOVERNMENT RIGHTS

This invention was made with Government support under Grant No. R21 EB013816, awarded by the National Institutes of Health. The Government has certain rights in the invention.

BACKGROUND OF THE INVENTION

Computed tomography (CT) outperforms all other diagnostic tests for the evaluation of many common clinical scenarios, including urgent trauma triage, the evaluation of abdominal pain, and the evaluation for inflammatory or ischemic bowel. The development of contrast material for CT imaging revolutionized medical imaging, particularly in the abdomen and pelvis where visceral organs show intertwined anatomy. Despite the proven value of contrast materials for CT, no substantially improved clinical agent has been introduced in the past 20 years. All commercial CT contrast materials are based on iodine (intravascular or enteric) or barium (enteric only).

A fundamental limitation of current clinical CT contrast materials is their inability to be distinguished from each other or from other radiodense structures such as shrapnel, calcifications, surgical staple lines or implants. Even with Dual Energy CT (DECT) or multi-energy CT, now an increasingly widespread clinical technology that allows material decomposition of imaged voxels based on differences in the X-ray attenuation caused by different materials when imaged with low and high X-ray spectra, iodine and barium-based contrast materials cannot be readily differentiated from each other because they have similar differences in X-ray attenuation when imaged with low and high X-ray spectra. For most DECT scanners, the low and high X-ray spectra are obtained at 80 kVp and 140 kVp tube potential settings, respectively. The difference in X-ray attenuation for an individual material in CT imaging when imaged at 80 and 140 kVp can be referred to as its 80:140 kVp CT number ratio. The 80:140 kVp CT number ratios of iodine and barium are virtually identical, which prevents accurate separation of contrast materials where the X-ray attenuation is primarily based on iodine and barium. This limitation causes clinical confusion and delays. For example, a CT scan enhanced with oral barium and intravenous iodine contrast that shows contrast leakage into the peritoneum may be ambiguous for whether the leak is due to bleeding (iodine), bowel perforation (barium), or urinary tract injury (excreted iodine), each of which is a clinical emergency but requires dramatically different management. To resolve such ambiguity, scans often must be repeated at the expense of lost time and therapeutic opportunity. Repeat CT scans also result in additional radiation dose. Increased public concern about CT radiation dose resulted in a 2011 NIH summit focused on CT dose reduction. CT scanners capable of multi-energy or spectral imaging are under development, but even with improved capability, these new CT technologies are unlikely to be able to readily differentiate iodinated from barium based contrast material.

The high value of enteric CT contrast is undisputed for the detection of extra-enteric fluid collections and masses in a wide range of disease. Tumors, abscesses, and hematomas that resemble bowel are well known diagnostic pitfalls in CT interpretation. Despite the value of enteric contrast, bright enteric contrast material paradoxically obscures intravenous contrast CT findings for some of the most devastating of diseases, including 1) Trauma where contrast material leakage may be ambiguous for being from vascular bleeding versus bowel lumen origin; 2) Bowel ischemia and infarction where bowel wall non-enhancement may be obscured by bright intralumenal enteric contrast material; 3) Bowel inflammation where bowel wall hyper-enhancement by IV contrast is the most reliable feature of active disease; 4) enteric bleeding where iodinated contrast extravasation into bowel or enhancing tumors is masked by the presence of enteric contrast; and 5) CT angiograms where enteric contrast limits three-dimensional reformations.

Further limitations of current enteric CT contrast material include toxicity and other complications. Barium-based agents may cause severe, potentially fatal peritonitis or aggravate infections at sites of leak, and may convert a partial bowel obstruction into a complete bowel obstruction. Iodinated agents may cause severe, even fatal pneumonitis when inadvertently aspirated and may also cause life threatening allergic-type reactions, and this concern limits its use in the up to 1% of patients with known prior reactions. This is likely related in part to the hyperosmolality of these agents. Moreover, several of these agents are brownish in color or poor-tasting. Some patients (up to 1-3%) have reactions to iodinated contrast material.

Development of a safe clinical enteric contrast material that can be used simultaneously with, but be differentiated from, iodinated and barium agents would immediately dramatically transform DECT imaging of trauma patients and millions of patients for a wide spectrum of diseases. Multiple bodily compartments could be injected and interrogated simultaneously for a single DECT or multi-energy CT examination to provide timely high resolution perfectly co-registered anatomic images of each system for rapid and confident diagnosis and will transform clinicians' ability to urgently and accurately evaluate multi-organ injury from trauma, invasive tumors, surgical complications, and inflammatory disease.

Non-iodinated materials tested for use with CT imaging include a broad range of high atomic-number (Z) elements: tungsten, tantalum, bismuth, the lanthanides such as gadolinium, and gold, among others [Yu S, Watson A. Metal-Based X-ray Contrast Media. *Chem Rev.* 1999; 99(9):2353-2378; and Mongan J, Rathnayake S, Fu Y, Wang R, Jones E F, Gao D W, Yeh B M. In vivo Differentiation of Complementary Contrast Media at Dual-Energy CT. *Radiology.* 2012; 265(1): 267-272]. Materials based on the low-atomic-number elements have not yet received attention or research interest for CT or DECT contrast enhancement applications.

With respect to image quality and utility, iodinated enteric contrast material cannot be readily differentiated from intravascular iodinated agents by DECT, except by context. Barium enteric contrast material cannot be readily differentiated from intravascular iodinated agents by DECT, except by context. Extravasation of barium from the bowel into surrounding tissue acts as an adjuvant and substantially exacerbates infections and abscesses. Extravasated barium may cause tissue granulation. Barium may flocculate (coat the bowel wall, often in a coarse heterogeneous pattern, and thereby cause imaging artifacts or confusing appearances of the bowel. Intravasated barium (barium that leaks out of damaged bowel and into the bloodstream) may cause micro emboli to the lung or liver and have prolonged retention. Barium suspensions separate readily and need to be shaken right before ingestion. Barium agents leave a chalky white residue in and around the mouth and on clothes.

An oral/enteric contrast agent that does not interfere with intravenous contrast agents for CT imaging of bowel wall enhancement/non-enhancement would cause a dramatic frame shift in the approach to CT imaging of the abdomen, and allow DECT to dramatically improve abdominal imaging. Dual energy CT is a relatively new technology, with practical clinical DECT scanners only available for less than 10 years. Currently, most radiologists give enteric contrast for routine abdominopelvic CT scans to distinguish bowel from other intraperitoneal structures (such as free fluid, loculated collections, ovaries, tumors). However, this enteric contrast obscures the bowel wall vascular enhancement/ nonenhancement, thereby reducing the effectiveness of CT for the evaluation of bowel inflammation, tumor, ischemia, and other pathology. Also, extravasated contrast material may be ambiguous as to whether it came from bowel, a blood vessel, or both. Currently, no feasible contrast material complementary to iodine- or barium based contrast materials are available.

BRIEF SUMMARY OF THE INVENTION

The present invention solves these and other problems by providing safe and effective formulations using low atomic-number compounds as enteric CT (or DECT) contrast materials suitable for human use. In various embodiments, the present invention provides the benefits of enteric contrast with CT without the pitfalls of current enteric contrast media. Benefits of oral contrast include: superior identification of enteric leaks, detection of extralumenal collections such as abscesses, detection of abdominopelvic tumors and masses, evaluation of intestinal transit time, evaluation of bowel obstruction transition point, superior evaluation for bowel wall thickening. Pitfalls of enteric contrast include: toxicity of iodinated or barium contrast material (see below), or when concurrent intravascular contrast material is given, obscuration of critically important findings for bowel mural ischemia or bowel inflammation, obscuration of abdomenopelvic vasculature, prevention of 3-dimensional reformations for CT angiography, ambiguity as to the origin of extravasated contrast material, and obscuration of active intraluminal gastrointestinal bleeding.

Use of a low atomic number agent has many benefits over use of most higher atomic number agents: 1) cost may be lower; 2) toxicity can be much lower; and 3) many low atomic number agents are already used in food or over the counter medications. Low atomic number agents can replace high atomic number agents for routine CT.

Enteric agents for CT are generally safer than injectable ones for several reasons: 1) Substantially lower doses and concentrations of enteric contrast are needed than intravascular agents. Typical intravenous iodinated agent administration requires up to 150 mL of 350 mg iodine/mL contrast (52 gram dose) for an abdominal CT scan. The typical oral dose is 800 mL of only 10 mg iodine/mL contrast (8 gram total iodine dose); 2) Very little contrast material is absorbed through the bowel wall into the vasculature; 3) Viscosity and osmolality are of minimal concern for enteric contrast materials; 4) Renal toxicity, which is seen with all intravascular agents, is unlikely with enteric agents; 5) Anaphylactoid and immune reactions are far less likely to occur with enteric than intravascular administration.

Moreover, the non-iodinated, non-barium enteric agent of the invention, when used for clinical CT, offers the advantage of allowing simultaneous administration of an enteric and intravascular or other bodily compartment agent, yet the agents can be readily differentiated from each other by dual or multi energy CT. Because the agents are administered such that they are imaged when they are simultaneously present in the body, in one embodiment, essentially complete co-registration of images of contrast enhanced regions is provided and the information available for evaluation is greater than if each contrast material were delivered and imaged separately and separate CT scans performed. Furthermore, in an exemplary embodiment, the radiation dose is half of what two separate scans would deliver. In various embodiments, the medium and formulations of the invention facilitate repeat CT scanning, reducing the ambiguity caused by previously delivered different-material based oral contrast.

The formulations and method of the invention also provide the advantage of reducing radiation dose due to reduced need for repeat/follow-up scans.

In an exemplary embodiment, the invention provides an enteric contrast medium formulation. An exemplary formulation comprises, (a) an enteric contrast medium comprising essentially water-insoluble particles of a material selected from microparticles and nanoparticles. Exemplary particles comprise a material comprising a plurality of atoms of an element with an atomic number from 6 to 52. In various embodiments, the particles are coated with a material compatible with enteric administration of the formulation to a subject in need of such administration. In an exemplary embodiment, the contrast medium is incorporated into a pharmaceutically acceptable vehicle in which the particles are formulated.

In an exemplary embodiment, the invention provides a contrast medium formulation that may also be delivered into other bodily cavities that may be natural such as the vagina or bladder, or surgically created such as neobladders, or artificial medical devices such as tubes, catheters, pouches, reservoirs, or pumps.

Additional illustrative advantages, objects and embodiments of the invention are set forth in the description that follows.

BRIEF DESCRIPTION OF THE DRAWINGS

FIG. 7 is a tabulation of an exemplary list of low-Z compounds of use as CT contrast materials in the invention.

FIG. 9. CT numbers at different X-ray tube potentials and 80:140 kVp CT number ratios of example inert materials. CT numbers were measured at tube potentials of 80, 100, 120, and 140 kVp on a commercial clinical CT scanner. Particles made from these exemplary materials serve as novel CT contrast agents differentiatable from iodinated or barium agents based on a large difference in their 80:140 kVp CT number ratio compared to those of iodinated or barium agents. Exemplary iodinated and barium agents are shown in the last two rows of the table.

FIG. 10. Exemplary silica microparticles and their CT number and 80:140 kVp CT number ratios. CT numbers were measured at CT tube potentials of 80, 100, 120, and 140 kVp on a commercial clinical CT scanner. All particles were suspended at concentrations of 35% (w/w) $SiO_2$ in water. Three types of silica microparticles were utilized: Crystalline silica (1-5 um diameter, US Silica); fused amorphous silica (3-5 um diameter); and spherical amorphous silica (1-2 um diameter). For each type of silica, three versions were formulated and tested: the original uncoated version of silica suspended in water; coated Version A, which is a PEG350 silane-coated silica suspended in water; and coated Version B, which is a PEG350 silane-coated silica suspended in an aqueous vehicle (5 wt % mPEG5000 and 3 wt % D-sorbitol) to improve suspension of the particles in water (absence of sediment/supernatant for the amorphous silica). Of particular note, the tested amorphous and fused silica microparticles have advantages over the tested crystalline silica because the extent of sedimentation and pellet formation for amorphous silica appear markedly lower than for the crystalline type in this test size range of 1-5 microns (note that both types of silica have similar specific gravity). The amorphous silica is a preferred choice because it is well known that crystalline silica is associated with a higher risk of carcinogenesis and pulmonary fibrosis than amorphous or fused silica.

Additionally, even larger diameter silica particles (50 microns, from Spectrum Chemicals Inc), uncoated or coated by PEG350 (or PEG2000), were found to sediment very easily after suspending in water, indicating the particle size dominates the suspension stability regardless of coating, which agrees well with theoretical calculations. A preferred size range is 1-5 microns in diameter, more preferably ~1 micron in diameter. A preferred formulation is a homogeneous and stable silica suspension.

FIG. 11. Exemplary low atomic number materials show similar CT number and 80:140 kVp CT number ratios when scanned on General Electric and Siemens dual energy CT scanners. CT numbers were measured at CT tube potentials of 80, 100, 120, and 140 kVp on commercial clinical dual energy CT scanners. For the General Electric instrument, the scanner was a 750 HD. For the Siemens instrument, the scanner was a Somatom Definition. The silica colloid (Ludox® TM-50) is 50% w/w in water from Aldrich Inc. The coated amorphous silica is a fused silica of 3-5 microns (Henan Hengxing Inc, China) coated with polyethylene glycol 350 silane as a 35% w/w suspension in distilled water. The amorphous spheric silica is 1-2 microns from American Elements Inc (Los Angeles, Calif.) and was suspended as 35% w/w in distilled water. Magnesium hydroxide is "Util-iMag H" from Martin Marieta Magnesia Inc (Baltimore, Md.) as a 60% w/w suspension of $Mg(OH)_2$ in water.

Figure 12:
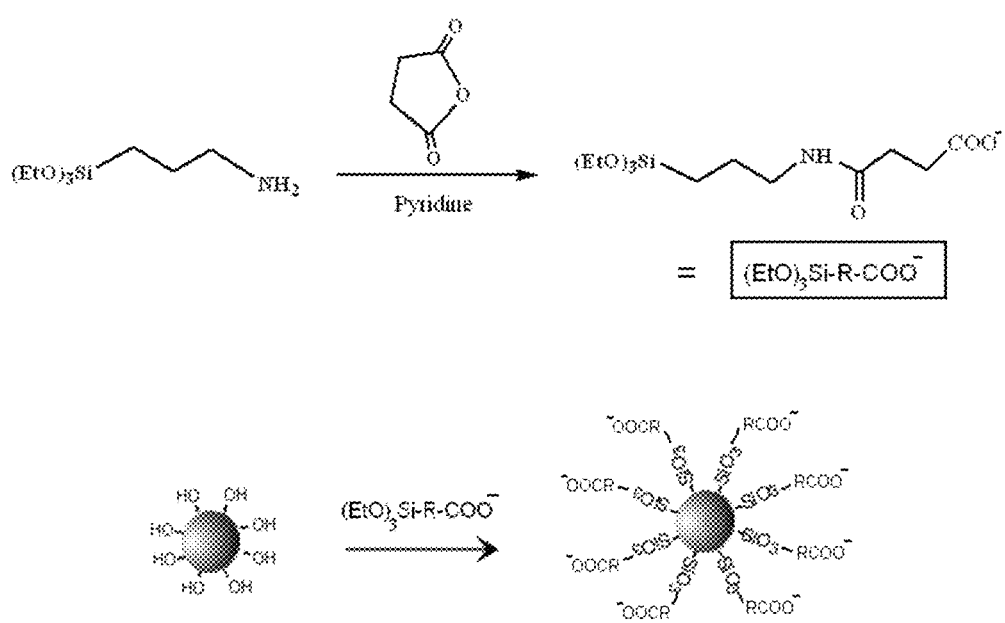

FIG. 12 is an exemplary scheme for surface coated silica microparticles by an anionic silane to produce a negatively charged coat.

DETAILED DESCRIPTION OF THE INVENTION

I. Introduction

Dual energy and spectral CT is a standard capability of modern scanners. Current dual energy technology allows simultaneous imaging of patients at two or more different tube potentials (such as 80 and 140 kVp). The X-ray energy spectra from these tube potentials can be further modified by selective filtering of the low or high kVp X-ray beam, such as by use of a tin filter, to achieve better spectral separation. Dual energy and spectral CT imaging can also be acquired using other methods, including sandwich detectors or photon counting which quantify the X-ray attenuation of different portions of an X-ray spectrum. Materials in the body are differentiated based on differences in their high to low tube potential CT number ratios (e.g. 80:140 kVp CT number ratios), which are related to the atomic numbers of the atoms in the material. A simulation of CT number ratios for a clinical CT scanner shows that iodine and barium exhibit near maximal 80:140 kVp CT number ratios for current clinical scanners, as measured by the Hounsfield Unit. Materials with more widely different ratios are more clearly differentiated by DECT, hence iodine and barium can be differentiated quite well from water or most soft tissues, which have 80:140 kVp CT number ratios of about 1.0. Ideal elements to incorporate into contrast material to allow differentiation from iodine and barium would have ratios close to 1.0 (correspond to high atomic numbers, e.g., between 71 and 83, or also low atomic numbers, e.g., between 3 and 20).

Materials that are imaged with dual energy or spectral CT can be digitally separated by related methods. The simplest is 2-material decomposition, whereby signal from each voxel is proportionally assigned to one or another material based on the 80:140 kVp (low energy to high energy) CT number ratio. This method generates two images, one which represents the signal assigned to one material, and the other which represents the signal assigned to the other material. A slightly more complex 3-material decomposition method can be used to separate three materials based on the 80:140 kVp (low energy to high energy) CT number ratios of three materials and on the assumption that the sum of the proportional densities of the three materials is 1.0. Multi-material decomposition can be obtained by iterative application of 3-material or 2-material decompositions to solve for CT signal contribution from 3 or more materials. All of these methods can also be used to generate virtual monochromatic CT images, which are extrapolated images that represent what the imaged object would have looked like at different monochromatic CT imaging, assuming that the object was composed entirely of the materials assumed in the material decomposition method.

Of the high atomic number elements, tantalum (Ta, Z=73), tungsten (W, Z=74), bismuth (Bi, Z=83) and gold (Au, Z=79) are among the least toxic. Gold is generally inert, but is too expensive to utilize for large volume contrast material. Nanoparticles or suspensions made of these elements have 80:140 kVp CT number ratios of between 1.0 and 1.2, are well suited to differentiate from iodinated (1.70) and barium (1.71) based contrast material, and are minimally toxic and likely meet the safety requirements needed for clinical use. Since the 80:140 kVp CT number ratios for such contrast materials are very similar to water and soft tissue, the commercial iodine versus soft tissue density material decomposition, available from every CT scanner vendor provide very good to excellent separation of iodine and the these agents even without contrast-specific software optimization—the signal from these agents is seen mostly, if not exclusively, in the "water/soft tissue" density map, but not the iodine map, on a two-material decomposition separation. A downside of these high-Z agents is that various compounds and formulations of each element have been previously described for use in X-ray or CT contrast material. A further downside of high-Z agents is their general high cost and concerns for patient safety.

Notably, low Z number elements have not been described as reporter atoms for CT or X-ray contrast material. However, the present invention provides safe formulations of low Z number elements (and compositions of these elements) providing safe and effective materials for enteric contrast agents. In exemplary embodiments, these formulations have 80:140 kVp CT number ratios between about 1.05 and 1.3. These materials are therefore readily differentiated from conventional commercially available iodinated and barium based contrast materials using simple two-material decomposition. Furthermore, the materials that have 80:140 kVp CT number ratios above about 1.2 may also be differentiated from water and soft tissue as well as iodinated/barium based contrast material by using three-material and multi-material decomposition. Potentially, further advances in CT technology will allow for greater ability to distinguish between materials with different X-ray absorption ratios at different X-ray energy spectra.

For medical diagnostic imaging, the X-ray attenuation coefficient, and thereby the CT number (a measure of CT signal) at a fixed concentration, of a contrast material increases exponentially with the effective atomic number of the material [R. C. Murry, Effective atomic numbers of heterogeneous materials, *Nature*. 1965; 207, 398-399]. The effective atomic number of a material depends greatly on the reporter atom(s), which are the atoms in the material that contribute the most to the X-ray attenuation of the material at imaging. Historically, only high atomic number reporter atoms such as iodine (Z=53) or barium (Z=56) have been used as reporter atoms for "positive" contrast materials, which are contrast materials with a substantially higher CT number than water or soft tissue. High concentrations of low-atomic-number materials have not been described for use with CT as a positive contrast material. For the first time, the present invention provides an effective, low-cost enteric contrast medium, and formulations of this medium, based on low-Z number elements for X-ray and CT imaging, including Dual Energy and spectral CT.

II. Definitions

Unless defined otherwise, all technical and scientific terms used herein generally have the same meaning as commonly understood by one of ordinary skill in the art to which this invention belongs. Generally, the nomenclature used herein and the laboratory procedures in organic chemistry, pharmaceutical formulation, and medical imaging are those well known and commonly employed in the art.

The articles "a" and "an" are used herein to refer to one or to more than one (i.e. to at least one) of the grammatical object of the article. By way of example, "an element" means one element or more than one element. Contrast agents with iodine, barium or other atoms with Z greater than 52 are exemplary "high Z" materials.

Designation as "high-Z" or "low-Z" materials is based on comparison of the reporter atom atomic number to the atomic number of iodine (Z=53) and barium (Z=56) which are the most commonly used reporter atoms in clinical contrast agents available for current CT and X-ray imaging.

A "disease" is a state of health of an animal wherein the animal cannot maintain homeostasis, and wherein if the disease is not ameliorated then the animal's health continues to deteriorate.

The term "half-life" or "t½", as used herein in the context of administering an enteric contrast medium of the invention to a patient, is defined as the time required for enteric concentration of a drug in a patient to be reduced by one half. There may be more than one half-life associated with the contrast medium depending on multiple clearance mechanisms, redistribution, and other mechanisms well known in the art. Further explanation of "half-life" is found in Pharmaceutical Biotechnology (1997, D F A Crommelin and R D Sindelar, eds., Harwood Publishers, Amsterdam, pp 101-120).

"Enteric contrast medium formulation" as herein used means, unless otherwise stated, a pharmaceutically acceptable liquid formulation for administration to a subject, which comprises at least one enteric contrast medium, and at least one pharmaceutically acceptable excipient suspending the medium, and which is prepared by dissolving or suspending an enteric contrast medium as herein described, e.g. in the form of a powder, emulsion or mash, in a pharmaceutically acceptable vehicle, before use for administration to the subject. Preferably the suspending medium is aqueous.

The term "residence time", as used herein in the context of administering an enteric contrast medium to a patient, is defined as the average time that the enteric contrast medium stays in the body of the patient after dosing.

The term "water-soluble" refers to moieties that have some detectable degree of solubility in water (e.g. >1 g/liter herein). Methods to detect and/or quantify water solubility are well known in the art. Exemplary water-soluble polymers include peptides, saccharides, poly(ethers), poly(amines), poly(carboxylic acids) and the like. Peptides can have mixed sequences or be composed of a single amino acid, e.g. poly(lysine). Similarly, saccharides can be of mixed sequence or composed of a single saccharide subunit, e.g., dextran, amylose, chitosan, and poly(sialic acid). An exemplary poly(ether) is poly(ethylene glycol). Poly(ethylene imine) is an exemplary polyamine, and poly(aspartic) acid is a representative poly(carboxylic acid).

"Poly(alkylene oxide)" refers to a genus of compounds having a polyether backbone. Poly(alkylene oxide) species of use in the present invention include, for example, straight- and branched-chain species. Moreover, exemplary poly(alkylene oxide) species can terminate in one or more reactive, activatable, or inert groups. For example, poly(ethylene glycol) is a poly(alkylene oxide) consisting of repeating ethylene oxide subunits, which may or may not include additional reactive, activatable or inert moieties at either terminus Useful poly(alkylene oxide) species include those in which one terminus is "capped" by an inert group, e.g., monomethoxy-poly(alkylene oxide). When the molecule is a branched species, it may include multiple reactive, activatable or inert groups at the termini of the alkylene oxide chains and the reactive groups may be either the same or different. Derivatives of straight-chain poly(alkylene oxide) species that are heterobifunctional are also known in the art.

As used herein, "pharmaceutically acceptable carrier" includes any material, which when combined with the conjugate retains the activity of the conjugate activity and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor, texture, and color additives or other ingredients. Compositions comprising such carriers are formulated by well known conventional methods.

As used herein, "administering" means oral administration, administration as a suppository, topical contact, intravenous, intraperitoneal, intramuscular, intralesional, intranasal or subcutaneous administration, intrathecal administration, or the implantation of a slow-release device e.g., a mini-osmotic pump, to the subject.

The term "enteric contrast medium" as used herein is understood to mean a dry or unsuspended component or mixture of components comprising at least one X-ray absorbing substance and optionally at least one pharmaceutically acceptable excipient, which may itself include other components, e.g., taste-masking agents, antioxidants, wetting agents, emulsifying agents, etc. The "dry suspension mixture" may subsequently be dissolved or suspended in a suspending medium to form the enteric contrast medium formulation of the invention. Terms such as "suspending medium" and "pharmaceutically acceptable excipient", as used herein, refers to the medium in which the component(s) of the enteric contrast medium are suspended.

The terms "coating" and "coated" as herein used are understood to include coatings which are biocompatible within an environment having an acidic, or a neutral, or a basic pH value.

The terms "particle" and "particles" as used herein refers to free flowing substances of any shape which are larger than about 1 nm, such as crystals, beads (smooth, round or spherical particles), pellets, spheres, and granules.

The term "taste-masked" as used herein refers to any formulation or particle, or oral pharmaceutical composition comprising an unpleasant tasting enteric contrast medium of the invention which has been treated to render it palatable and/or which does not substantially release the enteric contrast medium in the mouth, but rather for example in the stomach or the intestinal tract.

"An unpleasant and/or bitter taste" as used herein means that a majority of human patients judges the enteric contrast medium as having an unpleasant and/or bitter and/or extremely bitter taste after ingestion.

Current clinical CT scanners can generate different X-ray spectra for imaging. The energy spectra depend mainly on the tube potential (kVp) setting of the machine, and typically range from 80 to 140 kVp. These kVp settings result in CT scanners generating X-rays with a spectrum of energies, with the highest energy X-rays being 80 keV at a tube potential setting of 80 kVp, and 140 keV at 140 kVp. The X-ray spectra can be modulated, for example, by passing the X-rays through a filter such as aluminium, copper, or tin. For any given monochromatic X-ray energy passing through a known material, the extent of X-ray attenuation is defined by the Beer-Lambert law, and is proportional to a) the density of the atoms, b) the distance through the material which the X-ray passes, and c) the X-ray attenuation coefficient for that particular atom or material at that particular X-ray energy. Since the X-ray spectrum is relatively constant at any given kVp setting for a given scanner, the ratio of X-ray attenuation at 80 versus 140 kVp can be determined for any given material. Generally, iodine and barium have an 80:140 kVp CT number ratio of about 1.7 to 1.8 when imaged with a standard CT scanner using an aluminum or copper filter, though substantially higher 80:140 kVp CT number ratios may be obtained if a tin filter is used for the 140 kVp imaging (A. N. Primak, J. C. Ramirez Giraldo, X. Liu, L. Yu, and C. H. McCollough. Improved dual-energy material discrimination for dual-source CT by means of additional spectral filtration. Med. Phys. 36 (4), pp 1359-1369. April 2009). Water has, by definition, an 80:140 kVp CT number ratio of 1.0 since water is defined as having a CT number of 0 Hounsfield units for any given X-ray spectrum at CT. The elements of the periodic table have 80:140 kVp CT number ratios that range from about 0.9 to 1.8. Materials with more widely divergent 80:140 kVp CT number ratios are more readily distinguished at dual energy or spectral CT. Other methods for obtaining dual energy CT include the selection of different tube potential settings (e.g. 100 kVp and 140 kVp) and give similar results as for 80 and 140 kVp dual energy CT. Alternative methods for obtaining dual or multi energy CT are that the x-ray spectra may be modified to obtain greater separation of the energy spectra (e.g. by application of a tin filter to one of the kVp setting tubes) or other methods may be utilized to quantify the amount of absorption of different energy x-rays (e.g. sandwich detectors whereby the upper layer(s) of x-ray detectors block the low energy x-rays, thereby modulating the x-ray spectrum to which the lower layer(s) are exposed; photon counting detectors). These other methods still are of limited use to differentiate iodinated from barium-based materials, and can better differentiate materials with atoms of much different atomic number.

III. Embodiments

A. Compositions

In an exemplary embodiment, the invention provides an enteric contrast medium, and a formulation thereof readily differentiated from other currently available contrast materials. The invention is illustrated by reference to an enteric contrast medium formulation. An exemplary formulation comprises, (a) an enteric contrast medium comprising essentially water-insoluble particles of a material selected from microparticles and nanoparticles. Exemplary particles comprise a material comprising a plurality of atoms of an element with an atomic number less than 52, e.g., from 6 to 52, and preferably less than 30. In various embodiments, the particles are coated with a material compatible with enteric administration of the formulation to a subject in need of such administration.

In an exemplary embodiment, the elements making up the contrast medium optionally include an element having an atomic number from 12-39. Exemplary elements of use in the contrast medium of the invention include, without limitation, Mg, Al, Si, P, Ca, Sc, Ti, Fe, Zn, Br, Sr and Y.

In various embodiments, the element is selected for its ability to absorb or attenuate X-rays.

In an exemplary embodiment, the contrast medium is formulated into a pharmaceutically acceptable vehicle in which said particles are suspended. In an exemplary embodiment, the element is not silver (Z=47).

The population of atoms in the particles is variable and the correct elemental particle makeup is readily determinable by one of skill in the art. In an exemplary embodiment, the plurality of atoms comprises a first subpopulation of atoms having a first atomic number and a second subpopulation of atoms having a second atomic number. The first atomic number and the second atomic number are different atomic numbers.

One or more low-Z elements may be in combination with each other or with other atoms. For example, in one embodiment, the invention provides a material further comprising one or more atom selected from oxygen and sulfur forming a compound with said element. The contrast medium of the invention can include one or more carbon based components (e.g., ligands). In various embodiments, the contrast medium is selected from an oxide, a carbonate, a borate, a hydroxide, a phosphate, and a salt of an organic acid of the element.

In various embodiments, the enteric contrast medium of the invention includes a coating comprising a water-soluble polymer. As those of skill in the art appreciate, water soluble polymers appropriate for application in the present invention include, without limitation, a poly(alkylene oxide), a poly (amino acid), a poly(ester) polymer, a polysaccharide, a protein, polyvinylpyrrolidone, a poly(vinyl) polymer, a poly (ethylene imine) polymer, a poly(acrylic) polymer, a poly (siloxane) polymer, PAMAM dendrimers and other dendrimers, and a combination thereof, as well as those water-soluble polymers discussed hereinbelow.

Whether water-soluble polymers or otherwise, polymers incorporated into the contrast media of the invention can be of substantially any molecular weight. For example, polymers within the molecular weight range of from about 2 kd to about 1,000 kd daltons, e.g., about 1.5 kd to about 500 kd, e.g., from about 2 kd to about 100 kd, e.g., from about 3 kd to about 70 kd, are of use in the present invention.

In an exemplary embodiment, the coating comprises an organic molecule with a molecular weight of less than about 3 kd, less than about 2 kd or less than about 1.5 kd. In an exemplary embodiment, the coating comprises an organic molecule with a molecular weight of less than about 3 kd, less than about 2 kd or less than about 1.5 kd, which is a member selected from an organic acid (or alcohol, amine) and its derivatives or analogs, an oligosaccharide and a combination thereof.

In an exemplary embodiment, the coating is a protein, e.g., albumin.

Useful particles of the invention are found with specific sizes and within a range of sizes. In an exemplary embodiment, the diameter of the particles of the invention are from about 1 nm to about 500 microns, e.g., 1 nm to about 500 microns, e.g., 1 micron to about 50 microns encompassing each single diameter value and each diameter range within the larger range across all endpoints; in various embodiments, the particles are greater than about 50 microns. Further useful particle sizes include, for example, from about 5 microns to about 50 microns, e.g., from about 30 microns to about 50 microns.

The formulation of the invention can take the form of any sort of suspension, colloid, emulsion, or solution. When the formulation of the invention is a mixture with vehicle, the formulation is in a form selected from a suspension, a colloid, an emulsion, a hydrogel and a combination thereof. The formulations of the invention can include a single enteric contrast medium or two or more enteric contrast media. The media can be present in similar concentrations according to any useful measure of concentration. An exemplary embodiment includes different concentrations of one or more element in the contrast medium. Thus, in various embodiments, from about 10% (w/w, expressed as a weight percent, e.g. about 10 grams of contrast agent compound contained in about 100 grams of total contrast formulation) to about 90% (w/w) of the weight of said formulation is said particles. In an exemplary embodiment, the formulation includes about 30% (w/w) to about 50% (w/w) of the particles. The formulations of the invention include a population of particles of the invention suspended in a pharmaceutically acceptable vehicle. The vehicle includes any other useful component. For example, in some embodiments, the vehicle comprises an aqueous medium, and it further comprises an additive to impart a second property to the formulation, for example, retard dehydration of said formulation in the bowel, provide flavoring, stabilize the suspension, enhance flowability of the suspension, thicken the suspension, provide pH buffering and a combination thereof.

Notably, low Z number elements have not been described as the reporter atoms for CT or X-ray contrast material. However, in various embodiments, the present invention provides safe formulations of low Z number elements (and compositions of these elements) into safe and effective materials for enteric contrast agents, and exemplary formulations have 80:140 kVp CT number ratios between about 1.05 and about 1.4. These materials are therefore readily differentiated from conventional commercially available iodinated and barium based contrast materials using simple two-material decomposition. Furthermore, exemplary contrast media that have 80:140 kVp CT number ratios between about 1.2 and about 1.5 may also be differentiated from water and soft tissue as well as iodinated/barium based contrast material by using 3 material and multi-material decomposition.

Formulations of the invention are distinct both molecularly and functionally and can be recognized by both characteristics. For example, in one embodiment, the enteric contrast medium has an 80:140 kVp CT number ratio of less than or equal to about 1.7. Particles with exemplary useful values for this ratio include those with a ratio of from about 0.9 to about 1.7, e.g., from about 0.95 to about 1.4, e.g., from about 1.0 to about 1.3. This quantity is readily determinable for any contrast medium of the invention by one of ordinary skill in the art.

In various embodiments, the formulations of the invention are imaged on dual energy or spectral CT scanners which use different filters for the low and high kVp imaging, such as aluminum or copper filters for the low kVp images and tin filters for the high kVp imaging. Use of such selective filters allow for greater spectral separation of the low and high kVp X-ray imaging beams and allow for superior material decomposition separation of the formulation of the invention from conventional iodinated or barium contrast material and from water and soft tissue.

In an exemplary embodiment, the formulation of the invention includes a second contrast medium different from the first contrast medium. The second contrast medium can be soluble or insoluble in the pharmaceutically acceptable vehicle. When the second contrast medium is a particulate agent, the second contrast medium can include different atoms in the particulate core, a different coating, be of a different diameter, etc. relative to the first contrast medium. The second contrast medium can also be one or more of an iodinated, Ba-, Gd-, W-, or Ta-based contrast medium.

In an exemplary embodiment, the second contrast medium is a Mg-based medium, e.g., $Mg(OH)_2$.

Within the scope of the invention are formulations designed for single dosage administration. These unit dosage formats contain a sufficient amount of the formulation of the invention to provide detectable contrast in a subject to whom they are administered. In an exemplary embodiment, the unit dosage formulation includes a container holding sufficient contrast medium to enhance, in a diagnostically meaningful manner, a diagnostic image of a subject to whom the unit dosage has been administered. The container can be a vial, an infusion bag or any other appropriate vessel. The contrast medium may be in the form of a preformulated liquid, a concentrate, or powder. In an exemplary embodiment, the subject weighs about 70 kg. In an exemplary embodiment the image is measured through the abdomen of the subject, the pelvis of the subject, or a combination thereof.

Any of the formulations described herein can be formulated and utilized for administration through any of a variety of routes. Exemplary routes of administration include oral, rectal, intravaginal, intravascular, intrathecal, intravesicular, and the like.

High concentrations of low-atomic-number materials have not been described for use with CT as a positive contrast material. In an exemplary embodiment, the low-Z contrast materials in the formulation are highly concentrated, e.g., about 100 to about 900 mg/g, e.g., about 150 to about 500 mg/g, e.g., about 200 to about 300 mg/g) in terms of atoms of the X-ray attenuating element ("key atoms" or "reporter atoms"). In an exemplary embodiment, the particles account for from about 30% (w/w) to about 70% (w/w), e.g., from about 40% (w/w) to about 60% (w/w) of the formulation. The concentrations herein refer to those of the key element(s) in the contrast material that contribute to the majority share of the X-ray attenuation (absorption/scatter), usually but not necessarily the element with the highest atomic number within the molecule. X-ray attenuation is a function of the X-ray attenuation coefficient of the individual atoms for the X-ray spectrum times the concentration of the atoms in the contrast formulation.

Since low-Z materials do not attenuate the X-rays used for medical CT as well as high-Z materials such as iodine, barium, gadolinium, or other atoms, higher molar concentrations of low-Z materials are needed to produce similarly intense X-ray attenuation as high-Z materials at CT. Thus, in an exemplary embodiment, the invention provides a formulation of an enteric contrast agent having higher concentration of the low-Z element than that of a high-Z element in known enteric contrast medium formulations.

Contrast materials for imaging must be very safe for a wide range of patients and disease states. Whether patients are diseased or relatively healthy, all would benefit greatly from imaging studies that have low risk for injury and toxicity. In an exemplary embodiment, the invention provides an enteric contrast medium with an $LD_{50}$> about 5 g/kg would give a good safety margin, and would be comparable to the $LD_{50}$ of conventional iodinated or barium contrast agents.

In various embodiments, the contrast medium of the invention and preferably its formulation exhibits chemical stability across a wide pH range (e.g., from about 1.5 to about 9). The stomach exposes enteric contents to low pH of 1.5 and bile and small bowel may expose enteric contents to high pH of up to 9. Physicochemical stability is a critical component of safety and helps minimize the risk of reactions or adverse events. Adverse reactions may occur if excessive dissolution or degradation of the materials were to occur in the gastrointestinal tract, or if the breakdown products are potentially toxic.

In various embodiments, the invention provides a contrast medium and a formulation of a contrast medium with a $t_{1/2}$ that is sufficiently long to allow the completion of an imaging experiment with the concentration of the low-Z element remaining essentially undecreased within the region of interest. In various embodiments, the invention provides a contrast medium and a formulation having an in vivo residence time that is sufficiently short to allow essentially all of the administered low-Z atoms to be eliminated from the body of the subject before being altered (metabolized, hydrolyzed, oxidized, etc.) by the subject's body.

In various embodiments, the enteric transit time of the formulation is less than 12 hours in normal subjects. In an exemplary embodiment, the formulation includes sorbitol, polyethylene glycol or both to accelerate enteric transit times.

In an exemplary embodiment, the invention provides a contrast medium that dissolves slowly such that the majority of the administered low-Z atoms are eliminated via the gastrointestinal tract prior to being altered by the subject's body, and a dissolved or altered portion is excreted by the urinary tract. An exemplary embodiment is $Mg(OH)_2$ which has a low solubility of approximately 12 mg per liter, and free magnesium ions are quickly excreted by the kidneys into the urine in patients with normal renal function.

In an exemplary embodiment, the invention provides an enteric contrast medium which has an oxide core, e.g., a core of $SiO_2$. In various embodiments, the oxide core is coated. The core can be coated with a polymer or with small molecules as discussed herein. The underlying core is essentially non-toxic in a preferred embodiment. The toxicity of oxides such as $SiO_2$ is extremely low, with an enteric LD50 for $SiO_2$ being unmeasurable.

In an exemplary embodiment, the formulation of the invention avoids the risks associated with current homogeneous dispersion/formulation. For example, in current methods using current formulations, heterogeneous dispersion may cause imaging artifact that could be mistaken for or mask abnormal findings. Moreover, barium contrast agents have a tendency to flocculate or coat the mucosa of bowel, which can cause imaging artifact at CT.

The pharmaceutical formulation of the present invention may optionally include excipients and other ingredients such as one or more sweeteners, flavors and/or additional taste modifiers to mask a bitter or unpleasant taste, suspending agents, glidants, antioxidants, preservatives and other conventional excipients as needed.

The suspension of the invention may optionally include one or more antioxidants, if necessary, taste modifiers, sweeteners, glidants, suspending agents, and preservatives.

As will be appreciated, the above optional ingredients may be added to the powder formulation of the invention, and/or to the oral suspension of the invention.

Antioxidants suitable for use herein include any convenient agents known in the art for this purpose such as sodium metabisulfite, sodium bisulfite, cysteine hydrochloride, citric acid, succinic acid, ascorbic acid, sodium ascorbate, fumaric acid, tartaric acid, maleic acid, malic acid, EDTA with sodium metabisulfite or sodium bisulfite being preferred.

Antioxidants may be employed in an amount which will protect the formulation from oxidation as will be apparent to one skilled in the art.

Sweeteners for use in the formulations of the invention may be any convenient agents known in the art for this purpose and may be selected from any compatible sweetener groups such as natural sweeteners like sucrose, fructose, dextrose, xylitol, sorbitol, or manitol, as well as artificial sweeteners such as aspartame, acesulfame K and sucrolose. Xylitol and aspartame are preferred sweeteners.

Flavors and flavor modifiers or taste modifiers can also be used to further improve the taste and can be any convenient agents known in the art for this purpose and include, but are not limited to, orange flavor, apricot flavor, chocolate flavor, maple flavor, vanilla flavor, licorice flavor, orange vanilla flavor, creme de mint, cherry flavor, cherry vanilla flavor, berry mix flavor, passion fruit flavor, mandarin orange flavor, bubble gum flavor, tropical punch flavor, juicy compound for grape, grape flavor, artificial grape flavor, grape bubble gum flavor, tutti-frutti-flavor, and combinations thereof.

Suspending agents can be any convenient agents known in the art for this purpose and can be selected from xanthan gum, guar gum, hydroxypropylmethyl cellulose, hydroxypropyl cellulose, polyvinyl pyrrolidone, alginates, and sodium carboxylmethylcellulose with sodium carboxylmethylcellulose ("Na CMC") being preferred. Suspending agents may be employed in an amount within the range from about 0 to about 20% by weight of the powder formulation, and from about 0 to about 10% by weight of the oral suspension.

Preservatives can be any convenient agents known in the art for this purpose and can be selected from the group consisting of any compound compatible with drug actives such as methylparaben and propylparaben, benzoic acid, sodium benzoate, potassium sorbate, with methylparaben being preferred.

The invention also provides kits for use in a clinical and/or research setting. An exemplary kit includes: (a) a first vial containing the enteric contrast medium of the invention; and (b) directions for using and/or formulating the enteric contrast medium. In various embodiments, the kit further comprises a second vial containing a second contrast medium; and directions for administering and/or formulating the first and second enteric contrast medium in a clinical or research setting.

The contrast medium contained in the second vial can be soluble or insoluble in the pharmaceutically acceptable vehicle. When the second contrast medium is a particulate agent, the second contrast medium can include different atoms in the particulate core, a different coating, be of a different diameter, etc. relative to the first contrast medium. The second contrast medium can also be one or more of an iodinated, Ba-, Gd-, W-, Bi-, or Ta-based contrast medium.

In an exemplary embodiment, the second contrast medium is a Mg-based medium, e.g., $Mg(OH)_2$.

Activated particles useful in forming the coated contrast medium of the invention are discussed herein. The discussion focuses on preparing a particle which is activated and subsequently modified ("coated") with a modifying group (e.g., water-soluble polymer) for clarity of illustration. In particular, the discussion focuses on the preparation of modified sugars that include a poly(ethylene glycol) moiety. Those of skill will appreciate that the methods set forth herein are broadly applicable to the preparation of activated particles and their polymer conjugates, therefore, the discussion should not be interpreted as limiting the scope of the invention.

In general, the particle and the modifying group are linked together through the use of reactive groups, which are typically transformed by the linking process into a new organic functional group or unreactive species. Reactive groups and classes of reactions useful in practicing the present invention are generally those that are well known in the art of bioconjugate chemistry. Currently favored classes of reactions available to activate particles are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, ADVANCED ORGANIC CHEMISTRY, 5th Ed., John Wiley & Sons, New York, 2001; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from an activated particle or a modifying group include, but are not limited to:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with alkyl and acyl halides;

(h) amine or sulfhydryl groups, which can be, for example, acylated, alkylated or oxidized;

(i) alkenes, which can undergo, for example, cycloadditions, acylation, Michael addition, etc; and (j) epoxides, which can react with, for example, amines and hydroxyl compounds.

The reactive functional groups can be protected from participating in the reaction by the presence of a protecting group. Those of skill in the art understand how to protect a particular functional group such that it does not interfere with a chosen set of reaction conditions. For examples of useful protecting groups, see, for example, Greene et al., PROTECTIVE GROUPS IN ORGANIC SYNTHESIS, John Wiley & Sons, New York, 1991.

Figure 1:
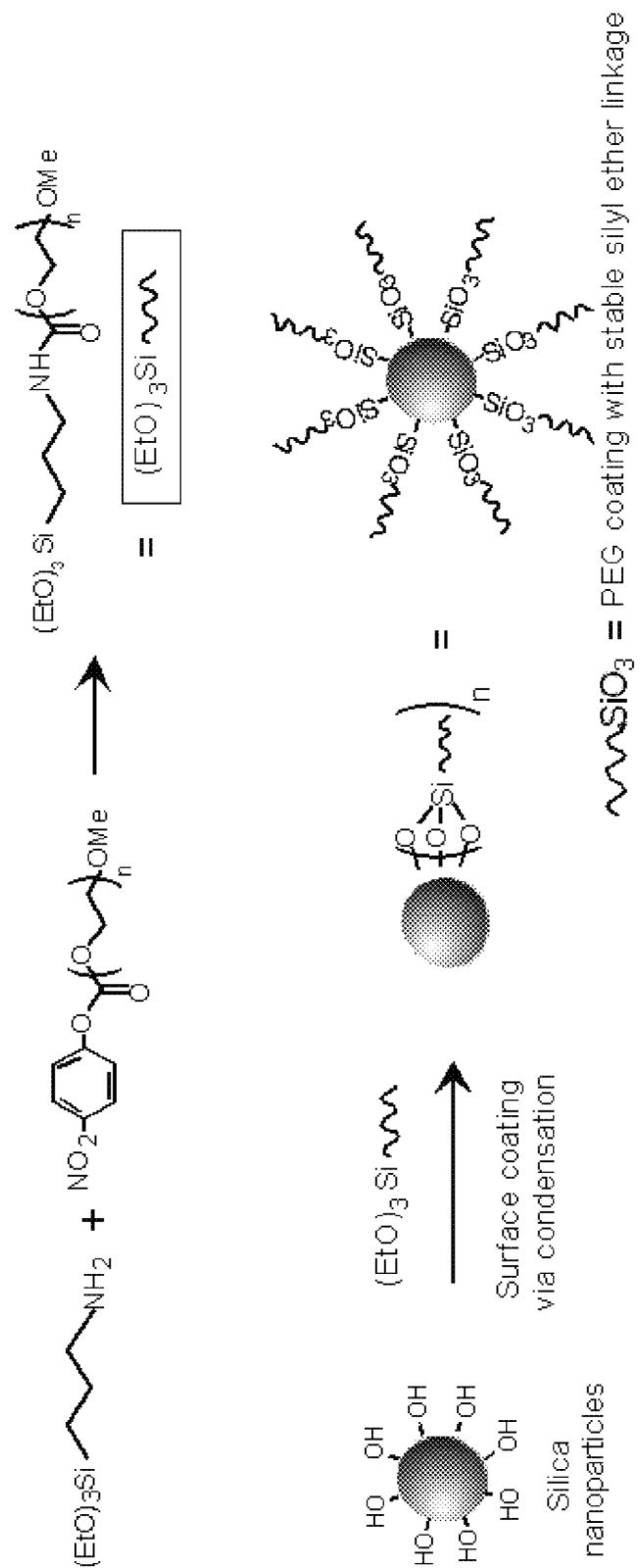
FIG. 1 is a polyethylene glycol-coated $SiO_2$ microparticle. The coating is via siloxane linkages.
Figure 2:
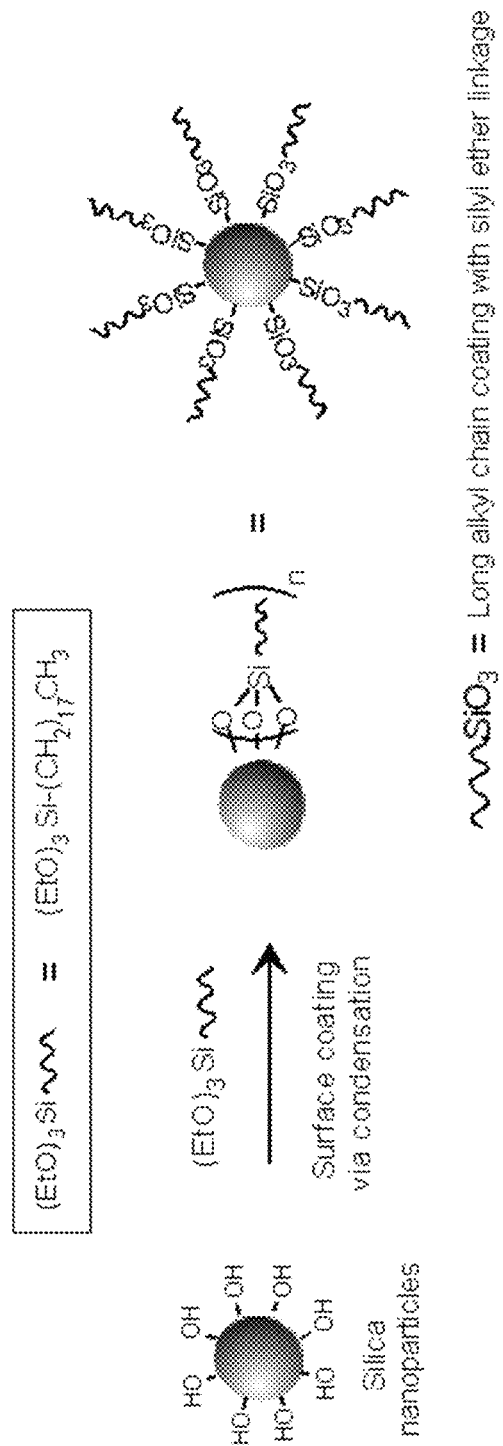
FIG. 2 is a long alkyl chain (C18)-coated $SiO_2$ microparticle. The coating is via siloxane linkages.
Figure 3:
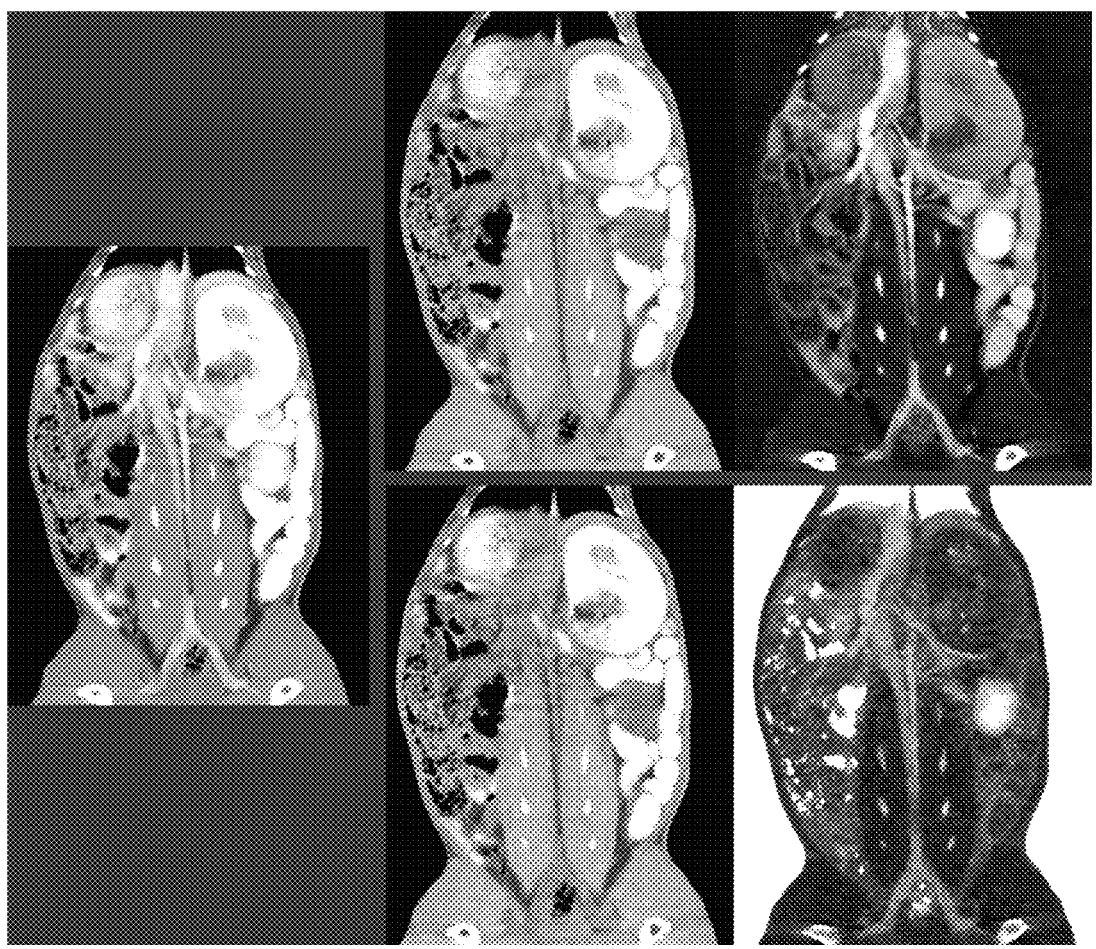
FIG. 3 shows two-material decomposition to differentiate silica enteric contrast from iodinated intravascular contrast at CT in a rabbit. On the conventional CT image (left-most image), enteric contrast material and intravascular contrast are difficult to distinguish except by context. Both materials appear white, indicating high X-ray attenuation. On the standard General Electric DECT two-material decomposition of the dual energy CT scan, the silica enteric contrast is seen on both the water map (top middle) and iodine map (top right image), thereby distinguishing it from iodinated intravascular contrast which is seen only on the iodine map. On the modified General Electric DECT two-material decomposition images (bottom row), the silica contrast material appears only in the silica map (bottom middle image) which also shows the soft tissue and water components of the image. The iodine map (bottom right) shows the intravascular iodinated contrast material. Note that the General Electric software, at this point, displays gas as bright white signal—further improvements in this commercial software can prevent this signal misassignment (see next figure).
Figure 4:
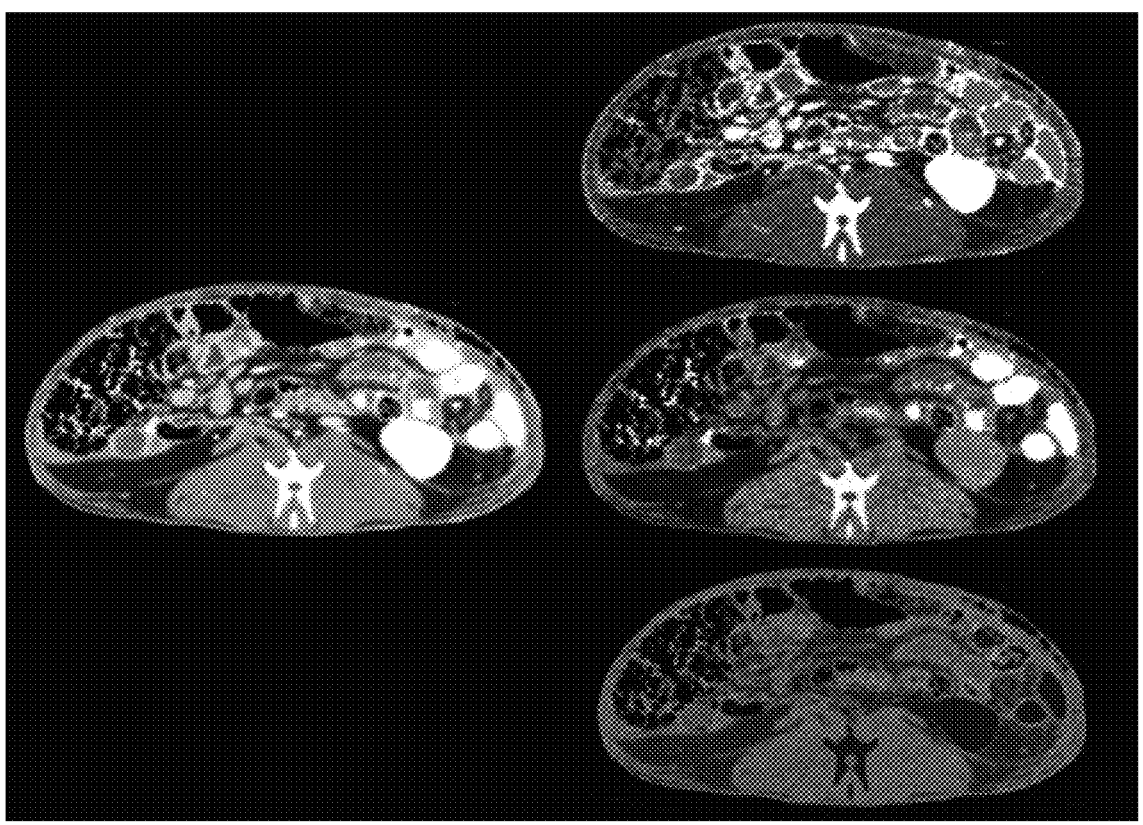
FIG. 4 shows three-material decomposition to differentiate silica enteric contrast from iodinated intravascular contrast at CT in a rabbit. On the conventional CT image (left middle image), enteric contrast material and intravascular contrast are difficult to distinguish except by context. Both materials appear white, indicating high X-ray attenuation. On the three-material decomposition of the dual energy CT scan performed using a modified software algorithm, the iodinated intravascular contrast map (top right image), silica enteric contrast map (middle right image), and soft tissue map (bottom right image) clearly show the different distributions of the two contrast materials. Bowel wall enhancement by intravascular contrast material is obscured in the conventional CT image, but is seen on the iodinated intravascular contrast map. The three-materials are readily differentiated and are perfectly co-registered. Owing to perfect co-registration, the information available for evaluation is greater than if each contrast material were delivered separately and separate CT scans performed. Furthermore, the radiation dose is half of what two separate scans would deliver.
Figure 5:
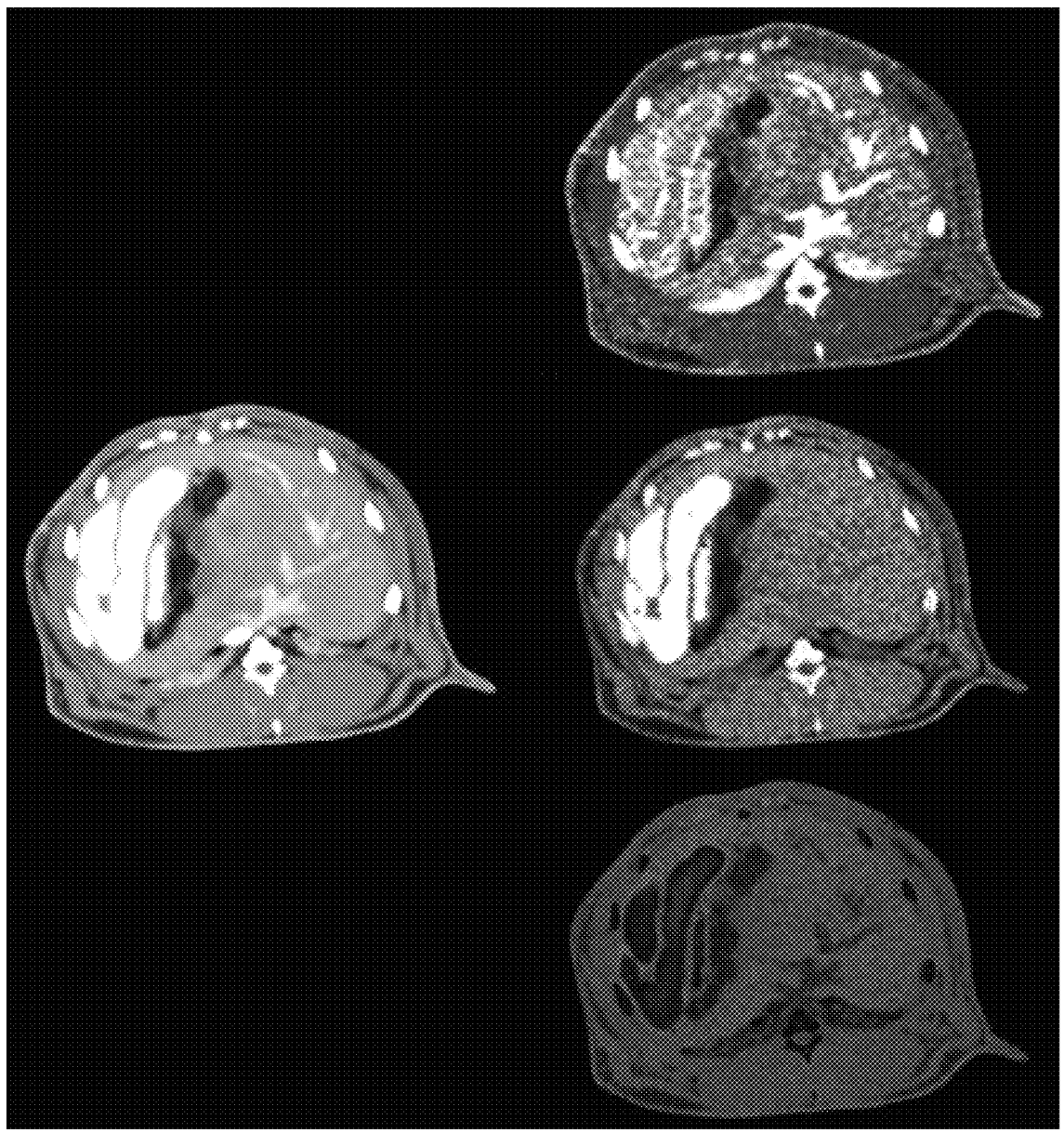
FIG. 5 shows a different rabbit evaluated using three-material decomposition to differentiate silica enteric contrast from iodinated intravascular contrast at CT. On the conventional CT image (left middle image), enteric contrast material and intravascular contrast are difficult to distinguish except by context. Both materials appear white, indicating high X-ray attenuation. On the three-material decomposition of the dual energy CT scan, the iodinated intravascular contrast map (top right image), silica enteric contrast map (middle right image), and soft tissue map (bottom right image) clearly show the different distributions of the two contrast materials. Bowel wall enhancement by intravascular contrast material is obscured in the conventional CT image, but is seen on the iodinated intravascular contrast map. The three-materials are readily differentiated and are perfectly co-registered. Owing to perfect co-registration, the information available for evaluation is greater than if each contrast material were delivered separately and separate CT scans performed. Furthermore, the radiation dose is half of what two separate scans would deliver.
Figure 6:
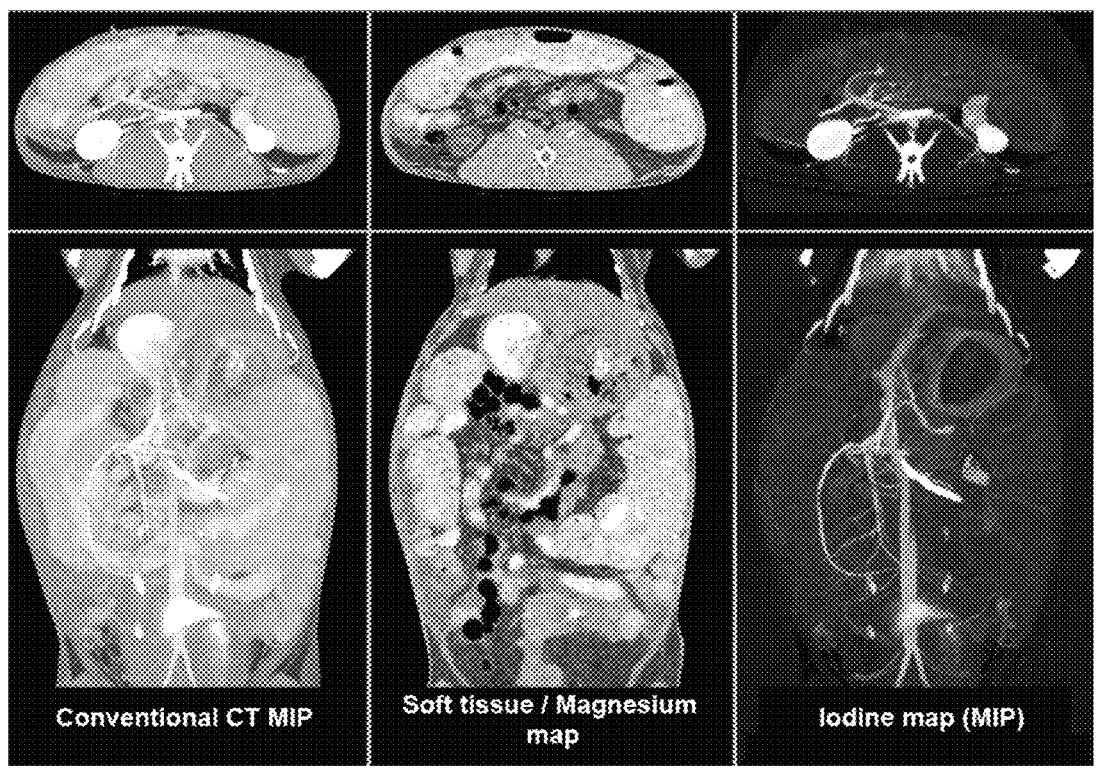
FIG. 6 shows two-material decompositions to differentiate $Mg(OH)_2$ enteric contrast from iodinated intravascular contrast at CT in a rabbit. The conventional CT (first column, transverse image on top, coronal image on bottom) shows a confusing appearance with both enteric Mg and intravascular iodinated contrast material superimposed on each other. The soft tissue/magnesium map shows the magnesium contrast material in the bowel without interfering signal from the intravascular iodinated contrast material. The iodine map (right column) shows a high resolution CT angiogram with detailed display of the blood vessels including small branches obscured by enteric contrast material in the conventional CT image. The iodine map also shows the bowel wall enhancement by iodinated contrast that was obscured by enteric contrast material in the conventional CT image. These latter displays are impossible to obtain by conventional CT when both conventional enteric and vascular contrast are delivered simultaneously. MIP=Maximum intensity projection.
Figure 8:
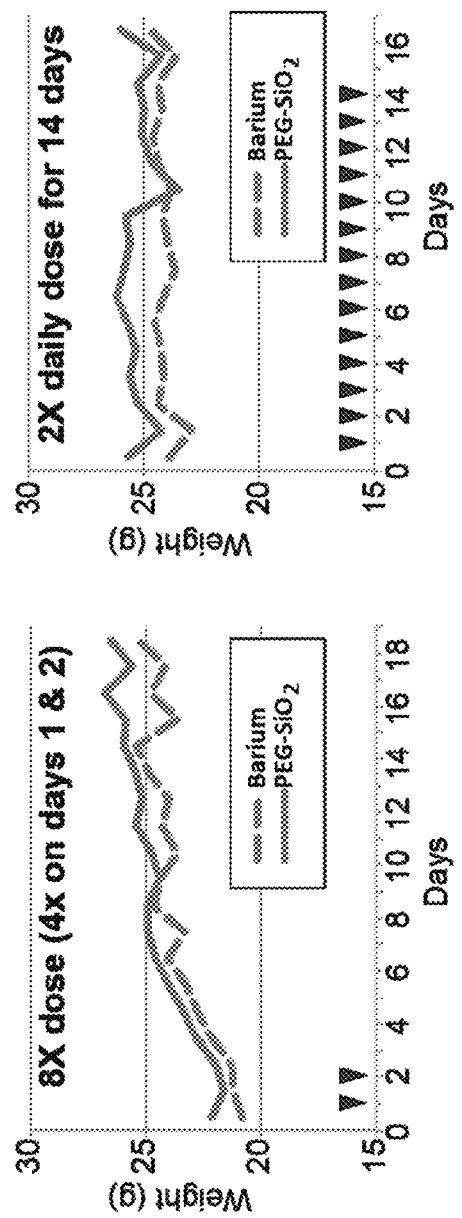
FIG. 8. High dose gastric gavage of barium 2.1% w/v or PEG-350 coated $SiO_2$ microparticles (as a 50% w/w suspension in a medium of 5% w/w PEG5000 and 3% w/w D-sorbitol) in Swiss-Webster mice in a non-GLP study. Each data point is average of 3 mice. No obvious toxicity was seen in mice after 4× dose on days 1 and 2 observed for a total of 19 days (left graph), or for mice given 2× daily dose for 14 days and observed for a total of 17 days (right graph). Within each cohort, no significant difference was seen in growth curve trajectories of SiO2-received mice compared to control mice (barium sulfate 2.1% w/v). No gross internal organ injury was seen in any mouse at sacrifice.

Exemplary routes to modified and coated particles are shown in FIG. 1 and FIG. 2.

The use of reactive derivatives of PEG (or other polymers or coatings) to attach one or more modifying group to the particle is within the scope of the present invention. The invention is not limited by the identity of the reactive PEG analogue. Many activated derivatives of poly(ethylene glycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl. Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

The particle coating of the invention may include one or more polymer. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known water-insoluble polymer is applicable to contrast medium of the present invention.

Representative polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly(ethylene terephthalate), poly(vinyl acetate), polyvinyl chloride, polystyrene, polyvinyl pyrrolidone, pluronics and polyvinylphenol and copolymers thereof.

Synthetically modified natural polymers of use in the contrast medium of the invention include, but are not limited to, alkyl celluloses, hydroxyalkyl celluloses, cellulose ethers, cellulose esters, and nitrocelluloses. Preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

In various embodiments, the particle is coated with one or more biodegradable or bioresporbable polymer. Representative biodegradable polymers of use in the particles of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly (α-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly(amino acids), poly(anhydrides), poly(orthoesters), poly (carbonates), poly(phosphazines), poly(phosphoesters), poly(thioesters), polysaccharides and mixtures thereof. More preferably still, the biosresorbable polymer includes a poly(hydroxy) acid component. Of the poly(hydroxy) acids, polylactic acid, polyglycolic acid, polycaproic acid, polybutyric acid, polyvaleric acid and copolymers and mixtures thereof are preferred.

B. Methods

The invention also provides methods of utilizing the formulations of the invention to acquire and enhance clinically meaningful CT images from a subject to whom the formulation of the invention is administered. Thus, in an exemplary embodiment, the invention provides a method of acquiring a contrast enhanced CT image of a subject. The method includes, administering to the subject a diagnostically effective amount of said enteric contrast medium formulation of the invention; and acquiring the CT image of the subject. In various embodiments, the enteric contrast medium has an 80:140 kVp CT number ratio of less than or equal to about 1.7 in said image in a DECT imaging experiment.

In an exemplary embodiment, the invention provides a contrast enhanced CT image of a subject through a region of the subject in which the contrast medium of the invention is distributed.

The image of the invention, and those acquired by the method of the invention utilize a contrast medium of the invention. The image is taken through any section of the body of the subject. In an exemplary method, the image is through the abdomen and/or pelvis of the subject.

The invention also provides methods for post-processing the CT images to digitally separate the CT signal produced by the contrast medium of the invention from CT signal produced by soft tissue, bodily fluid, or another contrast medium. In various embodiments, two-material decomposition or three-material decomposition or virtual monochromatic images and a combination thereof is used to separate the CT signal produced by contrast material of the invention from CT signal produced by another contrast medium or bodily tissues. In an exemplary embodiment of the invention, material decomposition image post-processing produces new CT images where the CT signal from the contrast material of the invention is highlighted or subtracted from the CT signal produced by the other contrast material or bodily tissues. In an exemplary embodiment of the invention, material decomposition image post-processing produces new CT images where the CT signal from a contrast material other than the contrast of the invention is highlighted or subtracted from the CT signal produced by the contrast material of the invention or bodily tissues.

In an exemplary embodiment, the contrast agent of the invention is imaged, after administration to a subject, using a dual energy or spectral CT scanner.

In various embodiments, the contrast agent of the invention is imaged, after administration to a subject, using a dual energy or spectral CT scanner with different material or thickness filters that modify the energy spectra of the X-ray beams. Exemplary materials to filter the energy spectra of the X-ray beams include but are not limited to aluminum, copper, or tin.

In an exemplary embodiment, the contrast agent of the invention is imaged, after administration to a subject, using a dual energy or spectral CT scanner and the images are post-processed to digitally separate the contrast agent from other contrast agents administered to the subject or from the subject's soft tissue.

In certain embodiments, the contrast agent of the invention is imaged, after administration to a subject, using a dual energy or spectral CT scanner and the images are post-processed to digitally separate the contrast agent from other contrast agents administered to the subject or the subject's soft tissue using 2-material; 3-material; or multi-material decomposition obtained from image or projection space CT data.

In various embodiments, the contrast agent is imaged, after administration to a subject, using a dual energy or spectral CT scanner and the images are post-processed to digitally separate the contrast agent from other contrast agents administered to the subject or the subject's soft tissue using virtual monochromatic images.

The invention also provides an embodiment in which the contrast agent of the invention is imaged, following administration to a subject, using a dual energy or spectral CT scanner and the images are post-processed to digitally separate the contrast agent from other contrast agents or from the subject's soft tissue using a combination of image or projection space CT data and virtual monochromatic images.

One of the advantages of the contrast media and formulations of the invention is compatibility with the administration of one or more additional contrast agents through any desired route. In various embodiments, the method further comprises administering to the subject a second contrast medium different from the enteric contrast medium. In various embodiments, the second contrast medium is administered through a route selected from intravascular administration, enteric administration, anal administration and administration into a different bodily cavity that is natural (e.g. vagina, bladder), surgically created (e.g. neobladder, ileal pouch), or artificial (e.g. medical device such as a catheter, reservoir, tube, or pump). A plurality of contrast materials may be administered to different bodily compartments. In an exemplary embodiment, the second contrast medium is an iodine- or barium-based medium, and a third contrast medium is a tantalum- or tungsten-based contrast medium.

In an exemplary embodiment, the first and second contrast agents are distinguishable from each other in an image set encompassing a region in which both first and second contrast media are distributed. An exemplary second contrast medium is an iodinated contrast medium.

The second contrast medium can be soluble or insoluble in a pharmaceutically acceptable vehicle. When the second contrast medium is a particulate agent, the second contrast medium can include different atoms in the particulate core, a different coating, be of a different diameter, etc. relative to the first contrast agents. The second contrast medium can also be one or more of an iodinated, Ba-, Gd-, W-, or Ta-based contrast medium.

In an exemplary embodiment, the second contrast medium is an iodine-based or barium-based medium.

The following Examples are offered to illustrate exemplary embodiments of the invention do not define or limit its scope.

EXAMPLES

Example 1

Silica Based Agents

The development of silica based contrast material started from commercially available $SiO_2$ particles including colloid nanoparticle materials (100-200 nm particle size), e.g. LUDOX or SYTON formulations at concentrations as high as 50 wt % of $SiO_2$ (Sigma-Aldrich Inc), which has a CT number of 670-520 HU at 80-140 kVp (CT scanner tube voltage), and a distinguishable 80:140 kVp CT number ratio of ~1.3 compared to iodinated contrast (80:140 kVp CT number ratio of ~1.7). These materials are highly stable at pH 9-10 as received, but were found to cross-link to become hard gels within one hour (pH 5.0) or within several hours (pH 7.0) after the pH is changed to the range of 2 to 7 (See, Iler R K. The chemistry of silica: solubility, polymerization, colloid, and surface properties and biochemistry. John Wiley & Sons, 1979, p 366). Use of a pH buffer like 50 mM carbonate buffer (pH 9.0) can apparently prevent the gelling but may not be able to reliably eliminate this serious safety risk in vivo. Therefore surface chemical modifications of these $SiO_2$ nanoparticles/microparticles were conducted to produce the formulations with chemical inertness or stability, using the safe and easily available/synthesizable coating reagents, see FIG. 1 and FIG. 2.

Chemical Modification Procedure

Method A

Monomethoxy PEG350 ("m-PEG", 8.9 g, Sigma-Aldrich) was dried by azeotropic distillation with anhydrous benzene, then was dissolved in anhydrous dichloromethane (100 mL) and cooled to 0° C. To this cooled solution was added 4-nitrophenyl chloroformate (10.1 g in 25 mL of dichloromethane), followed by addition of anhydrous pyridine (30 mL). After an overnight reaction at 0-5° C., the mixture was concentrated at a ratorary evaporator (water bath 40° C.) to about 50 mL, and the product was precipitated by adding anhydrous ether (200 mL) then cooling down to −20° C. for half an hour. The precipitate was filtered, washed by cold ether then dried in vacuum, giving a white solid as the m-PEG350 monocarbonate (yield 11.6 g).

To a solution of the m-PEG350 monocarbonate above (7.5 g) in anhydrous chloroform (50 mL), 3-aminopropyl triethoxysilane (3.2 g) was added. The mixture was stirred at room temperature for 4 hrs, with exclusion of moisture. When the reaction was complete, the yellow solution was evaporated to ~20 mL, then anhydrous ether (100 mL) was added to produce a syrupy product. The syrup was redissolved in chloroform (15 mL) and precipitated again by ether, and dried in vacuum to afford a slightly yellow syrup (8.1 g) as the m-PEG350-triethoxysilane coating reagent. Its structure was confirmed by H-1 NMR (400 MHz, $CDCl_3$): 0.6, 1.7, 2.9 ppm ($SiCH_2CH_2CH_2N$), 1.1 and 3.9 ppm ($OCH_2CH_3$), 3.6 ppm (PEG). Similarly, m-PEG2000-triethoxysilane was synthesized and characterized.

Silica nanoparticles (100 g amorphous $SiO_2$, precipitated with acetone from commercial LUDOX silica colloid, Sigma-Aldrich, 100-200 nm) was mixed with 200 mL N,N-dimethylformamide with moderate stirring at room temperature. The PEG-triethoxysilane reagent (5.0 g, the amount depending on the specific surface area of the particle thus particle size) was added to the suspension mixture. With vigorous stirring, to this suspension was added dropwise a freshly mixed solution of ammonia (29.1%, 10.0 mL) in 20 ml of DMF with a dropping funnel in 30 min. The coating reaction was continued for 24 hrs at room temperature. After standing for half an hour, the supernatant was discarded, then acetone (~200 mL) was added to completely precipitate the coated silica particles. The crude particle product was isolated by centrifugation (1 min, 3000 rpm), then resuspended in acetone for another washing cycle. This purification procedure was repeated for 3-4 times until no ammonia was detected by tests on wet pH papers. The resulting slightly yellow precipitate was further washed by distilled water for 4-5 cycles till no PEG-silane reagent in the supernatant was detected by UV (210 nm), each wash cycle consisting of centrifugation (1 min) and resuspension in water by votexing (30 seconds). After washing by acetone then vacuum drying of the precipitate, PEG350-coated silica microparticles was obtained as a white powder (yield 80.6 g). H-1 NMR of a concentrated suspension of coated silica (35% w/w in $D_2O$) confirmed the existence of PEG coat (3.6 ppm) on the particles.

Chemical inertness confirmation: a suspension of the PEG-coated silica microparticle product (2 g) in 2 g of distilled water was prepared, then its pH was adjusted to 5.2. No gelling was ever observed during 14 days. A side-by-side control experiment with the non-modified silica colloid (LUDOX-50) gave a hard gel in just 60 minutes after its pH was adjusted to 5.2 from originally pH 9 as received. This elimination of crosslinking reactivity confirmed the successful PEG coating on this nanoparticle. Its properties are listed below.

Formulation:
300-500 mg $SiO_2$/gram in distilled water or 3% sorbital solution or 1-2% methylcellulose solution.
X-Ray Attenuation:
Same as the non-coated $SiO_2$ formulations at the same concentrations.
80:140 kVp CT Number Ratio:
Same as the non-coated $SiO_2$ formulations (~1.3).
Chemical Stability:
No gelling effect was observed at pH between 1.5 to 9.0;
No instant precipitation was found by adding 1 M NaOH solution, as was observed for the non-coated silica nanoparticle colloids due to existence of abundant silanol groups.
Physical Stability of Aqueous Suspension:
No significant precipitation appeared for >3 hrs at room temperature after vortexing or stirring.

Method B

Crystaline silica Min-U-Sil-5 (average particle size 1.4 micron, US Silica Inc, Frederick, Md.) was soaked in 0.5 N HCl for 2 hours then washed by distilled water by centrifuging till the supernatant is pH-neutral and chloride-free. The precipitate was then washed by acetone and further dried in vacuum. This step is to activate the surface silanol groups as well as removing possible water-soluble impurities.

Crystaline silica treated above (100 g, about 1.4 micron particle size) was mixed with 300 mL of acetone with vigorous stirring, then a small amount of water (1.0 mL) was introduced. With vigorous stirring, the addition of PEG350-triethoxysilane reagent (3.0 g) was added, followed by addition of 3-4 drops of ammonia solution (29%), the reaction was kept at room temperature for 24 hours. Thereafter 6.0 mL of 29% ammonia was added to the mixture, the stirring was continued for 30 min. After the reaction was completed, the post-processing procedure was conducted similarly to that in Method A described above.

Similarly, amorphous fused silica microparticles (3-5 micron, Henan, China) and synthesized amorphous, spheric silica microparticles (1-2 micron, American Elements Inc, Los Angeles, Calif.) were coated with PEG350-silane as described above.

Method C

Introducing large-molecular-weight PEG coating (e.g., PEG2000). Crystaline silica Min-U-Sil-5 (average particle size 1.4 micron, US Silica Inc, Frederick, Md.) was pretreated and purified as described above (see Method B).

Crystalline silica treated and dried above (100 g, about 1.4 micron particle size) was mixed with 200 mL of dry DMF with vigorous stirring. To the suspension mixture was added the PEG2000-triethoxysilane reagent (12.5 g). The mixture was heated to 80-85° C. then kept at this temperature for 24 hours. After the mixture was cooled down to room temperature, ammonia solution (6.0 ml, 29% w/w) in 20 ml DMF was added dropwise in 30 min, then the reaction was continued for additional 6 hours at room temperature. After the reaction was completed, the post-processing procedure was conducted similarly to that in Method A (or Method B).

Similar chemical modification scheme to the one described in FIG. 1 above except using a different, commercially available C-18 type hydrophobic silanization reagent, namely octadecyltriethoxysilane (FIG. 2).

Similar chemical modification scheme to the one described in above except using a synthesized, hydrophilic, but anionic silanization reagent (FIG. 12), intended to introduce negative charges on the silica particle surface in order to improve the physical stability of the silica microparticle suspension. The coating procedure is similar to Method A or B described above.

Of note, this anionic silane was readily synthesized from commercially available chemicals. The aminopropyltroiethoxysilane (5.5 g) was dissolved in 30 mL of anhydrous THF. To this solution, succinic anhydride (2.9 g) and pyridine (2 mL) were added sequentially with stirring. The reaction lasted for 4 hours at room temperature. After rotary evaporation under reduced pressure (water bath<50° C.), the residue was dried in vacuum to yield a syrupy product (10.5 g), the structure of which was confirmed by H-1 NMR (400 MHz, $D_2O$): 0.6, 1.6, 3.0 ppm ($SiCH_2CH_2CH_2N$), 1.2 and 3.9 ppm ($OCH_2CH_3$), 2.5 ppm ($COCH_2CH_2CO$).

Example 2

High-Concentration $Mg(OH)_2$ Particulate Formulation

Common magnesium-containing over the counter medications include $Mg(OH)_2$ which is a good choice as a low-Z contrast material platform, but the available over the counter medication concentrations are too low (in the range of tens milligrams of Mg per mL) for effective use as CT contrast material. High-concentration Mg-based formulations are therefore needed. One example is a high-concentration $Mg(OH)_2$ suspension, which was successfully tested in a rabbit model without observing obvious toxicity or discomfort, probably due to its low solubility in water. The $Mg(OH)_2$ was diluted as a 400-HU homogeneous suspension from an originally 60 wt % suspension (namely, 60 g magnesium hydroxide in 100 g of formulated homogeneous suspension which was obtained commercially and measured ~700 HU at 80 kVp at CT). The benefit of $Mg(OH)_2$ microparticles is that dissolution is slow, and so systemic exposure to Mg is low. Furthermore, absorbed Mg is readily excreted by the kidneys when normal renal function is present, thereby minimizing the risk of systemic toxicity. The most common side effects of enteric $Mg(OH)_2$ are diarrhea and dehydration. Notably, relatively high dose intravenous magnesium in the form of magnesium sulfate ($MgSO_4$) is given clinically for preeclampsia and as a tocolytic to slow down the process of labor and has been shown to be safe for mother and fetus. Dosages of intravenous $MgSO_4$ are approximately 6 g loading dose then 1 to 2 g/hour, which is equivalent to 1.2 g Mg loading dose and 0.2 to 0.4 g Mg per hour. The systemic absorption of Mg from $Mg(OH)_2$ would likely be hundreds of times lower than what is seen with such $MgSO_4$ treatment due to the low water-solubility of $Mg(OH)_2$ at the physiological neutral pH range. The expected typical dose of Mg needed for oral contrast is ~160 g Mg (800 mL of 40 wt % $Mg(OH)_2$ with specific gravity of 1.3) The expected dissolution rate of $Mg(OH)_2$ in aqueous solution without modification is very low since the solubility of this agent is 12 mg/liter at room temperature. Since the volume of the bowel is approximately 3 liters, the maximum Mg absorption across the bowel would not reach any significantly concerning level, particularly since free intravascular Mg ions are readily and rapidly excreted into the urine in patients with normal renal function.

To further optimize the formulation, the dissolution of $Mg(OH)_2$ can be further slowed by delivering it with a buffer or antacid (like minimum amount of carbonate, sodium salt) to neutralize the acidic environment of the stomach, or with a proton pump inhibitor to prevent the generation of acid in the stomach.

Example 3

A computer simulation demonstrated that contrast agents containing atoms with a high (Z=70 to 82) or low (Z<25) atomic number as the reporter atom can theoretically be outstanding complements to iodine- or barium- (Z=53 and 56, respectively) based contrast agents. Notably, the only currently clinically available CT contrast materials utilize iodine or barium as the reporter atom. Contrast agents with these high or low atomic number reporter atoms show markedly different CT X-ray number ratios for low and high kVp settings compared to iodine- or barium-based contrast material. Iodine- and barium-based contrast materials show an 80:140 kVp CT number ratio ("80:140 kVp ratio") of approximately 1.75. The high and low atomic number agents should show 80:140 kVp ratios of <1.35. Notably, the 80:140 kVp ratio of water is by definition 1.0. Iodine- and barium-based contrast materials have the highest theoretical 80:140 kVp ratios of the elements on the periodic table. Of note: for conventional CT scans, contrast materials all look the same—they all cause increased X-ray attenuation when present and cannot be distinguished except by context.

In vitro experiments demonstrated that the concentrations of two contrast materials with markedly different 80:140 kVp ratios can be much more accurately quantified with DECT compared with contrast agents with similar 80:140 kVp ratios to each other when mixed solutions with different concentrations of the paired contrast materials are created. In other words, the concentrations of iodine- and barium-based agents, which are contrast materials with very similar 80:140 kVp ratios, could not be quantified with much accuracy when both materials are imaged in the same CT scan. However, concentrations of iodine- and tungsten-based contrast materials could be quantified in mixed solutions with only 4% error. Of note, for conventional CT scans, two different contrast materials cannot be distinguished/quantified when mixed.

In vivo experiments in a rat model showed that serially injected intravascular contrast agents (tungsten-then iodine-based) can be distinguished by DECT in different portions of the vascular bed (one in the arterial, and one in the venous/bloodpool phase of enhancement) at CT, and thereby allow multiphasic CT scans to be obtained with a single DECT scan, thereby improving diagnostic value while simultaneously reducing radiation dose to the subject (for conventional CT, multiphasic exams require multiple CT scan acquisitions timed to when the intravascular contrast material is predominantly in the arterial system, and then again in the venous system).

It was shown in a rabbit model that paired complementary contrast agents with markedly different 80:140 kVp ratios, one contrast material in the bowel and one intravascular, could be readily distinguished by DECT such that the enhancement of the bowel wall by intravascular contrast material could be visualized despite the presence of dense complementary contrast material in the bowel lumen. Of note: for conventional CT where both enteric and intravascular contrast material is present, the extent of bowel wall enhancement by intravascular contrast material cannot be visualized when dense enteric contrast material is present. It was also shown that 3 or more different contrast agents (for example, iodine, gadolinium, tungsten-based) can be differentiated at DECT, such as when the iodine-based is in the blood vessels, gadolinium-based is in the bladder, and tungsten-based is in the bowel).

Also of note for the above model, it was shown that enteric contrast material could be made from concentrated suspensions/colloids of low atomic number materials, including magnesium hydroxide, aluminum hydroxide, and silica (silicon dioxide). This is a highly novel finding. All clinical and preclinical X-ray contrast materials published/available utilize moderate to high atomic number atoms (iodine, barium, gold, tantalum, bismuth, tungsten, thorium, and others). The reason low atomic number agents had not been developed/describe previously may be due to differences between plain film X-ray, for which contrast material was historically developed, and CT. CT has much greater (10× or more) sensitivity for detecting contrast material. As such, the relatively low level X-ray attenuation caused by low atomic number agents do not show up well at plain film radiography and thus were not considered in the past. Lower concentrations of high atomic number agents block/attenuate X-rays much more readily than do low atomic number agents. Also, it is non-obvious to researchers in the field including most chemists how to make unusually concentrated, stable suspensions/colloids of these lower atomic number agents compared to making relatively less concentrated suspensions/colloids of the higher atomic number agents. The use of very high physical densities or concentrations of low atomic number agents for use as CT contrast material were not previously described. The benefit of using low atomic number agents is that many of these agents are extremely cheap and known to be of very low toxicity for enteric use (milk of magnesium is an over the counter medication with minimal toxicity. Silica is of very low toxicity, especially if rounded/ovoid/amorphous particles are used and in solution. (silicosis may occur if rod-like particles are used as a powder and inhaled).

It was demonstrated in a DECT rabbit abdominal trauma model that paired complementary CT contrast material, with one in the bowel and one intravascular, can markedly increase the sensitivity and specificity of determining whether extravasated contrast material were from a bowel leak versus a vascular leak versus both. First year resident radiologists in training shown DECT images of these rabbits outperformed experienced faculty abdominal trauma radiologists who only had conventional CT images for accuracy in diagnosing the source of extravasated contrast material. Furthermore, experienced faculty radiologists showed improved performance when shown the DECT images compared to when only conventional CT images were shown. It was also demonstrated that bowel wall enhancement by intravascular iodinated contrast material could be determined for bowel containing low atomic number enteric contrast material, but not for bowel containing iodine- or barium-based enteric contrast.

The present invention has been illustrated by reference to various exemplary embodiments and examples. As will be apparent to those of skill in the art other embodiments and variations of this invention may be devised by others skilled in the art without departing from the true spirit and scope of the invention. The appended claims are to be construed to include all such embodiments and equivalent variations.

The disclosures of each and every patent, patent application, and publication cited herein are hereby incorporated herein by reference in their entirety.

What is claimed is:

1. A method of acquiring a contrast enhanced X-ray computed tomography image of a subject's gastrointestinal tract, said method comprising:
(a) orally administering to said subject a diagnostically effective amount of an enteric contrast medium formulation comprising:
(i) a plurality of non-iodinated, non-barium, water-insoluble particles of the enteric contrast medium, selected from microparticles and nanoparticles, consisting of a core of an oxide of a single element with an atomic number from 12-39,
wherein a region of the image of the subject's gastrointestinal tract containing said enteric contrast medium has an 80:140 kVp CT number ratio from about 0.9 to about 1.4 and
wherein said particles are coated with a polymer which is a member selected from a poly(alkylene oxide), a poly(amino acid), a poly(ester) polymer, a polysaccharide, polyvinylpyrrolidone, a poly(vinyl) polymer, a poly(ethylene imine) polymer, a poly(acrylic) polymer, a poly(siloxane) polymer, a protein, a dendrimer and a combination thereof,
said particles constituting from about 30% (w/w) to about 70% (w/w) of said formulation; and
(ii) a pharmaceutically acceptable vehicle in which said particles are dispersed; and
(b) acquiring said X-ray computed tomography image of said gastrointestinal tract of said subject, wherein said image is an image of a region selected from the abdomen and pelvis of said subject.

2. The method according to claim 1, wherein said oxide of a single element is silicon oxide.

3. The method of claim 1, wherein said coating comprises poly(alkylene oxide).

4. The method of claim 1, wherein said polymer has a molecular weight of less than about 3,000 daltons.

5. The method of claim 1, wherein the size of said particles is from about 1 nm to about 500 microns.

6. The method of claim 5, wherein the size of said particles is from about 1 micron to about 50 microns.

7. The method of claim 1, wherein said enteric contrast medium has an 80:140 kVp CT number ratio from about 1.3 to about 1.4.

8. The method of claim 1, wherein said enteric contrast medium has an 80:140 kVp CT number ratio from about 0.9 to about 1.3.

9. The method of claim 1, wherein said formulation is an unit dosage oral formulation.

10. The method according to claim 1, wherein said method further comprises administering to said subject a second contrast medium different from said enteric contrast medium, and said second contrast medium is administered through a route selected from oral administration, intrathecal administration, intravesicular administration, enteric administration, anal administration and intravascular administration.

11. The method according to claim 10, wherein said second contrast medium is a member selected from an iodinated contrast medium, a Ba-, Gd- W-, Bi-, and a Ta-based contrast medium.

* * * * *